US008758904B2

(12) United States Patent
Fukumatsu et al.

(10) Patent No.: US 8,758,904 B2
(45) Date of Patent: *Jun. 24, 2014

(54) ORGANIC ELECTROLUMINESCENT DEVICE COMPRISING A FIRST ELECTRON-TRANSPORTING LAYER AND A SECOND ELECTRON-TRANSPORTING LAYER

(75) Inventors: Takayuki Fukumatsu, Kitakyushu (JP); Toshihiro Yamamoto, Kitakyushu (JP); Katsuhide Noguchi, Kitakyushu (JP); Ikumi Ichihashi, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 260 days.

This patent is subject to a terminal disclaimer.

(21) Appl. No.: 12/922,979

(22) PCT Filed: Feb. 27, 2009

(86) PCT No.: PCT/JP2009/053713
§ 371 (c)(1),
(2), (4) Date: Oct. 27, 2010

(87) PCT Pub. No.: WO2009/116377
PCT Pub. Date: Sep. 24, 2009

(65) Prior Publication Data
US 2011/0037062 A1   Feb. 17, 2011

(30) Foreign Application Priority Data

Mar. 17, 2008 (JP) ................................. 2008-067565

(51) Int. Cl.
*H01L 51/50* (2006.01)
*C09K 11/06* (2006.01)

(52) U.S. Cl.
USPC .............. 428/690; 428/917; 313/506; 257/40

(58) Field of Classification Search
None
See application file for complete search history.

(56) References Cited

U.S. PATENT DOCUMENTS

| 5,942,340 | A | 8/1999 | Hu et al. |
| 5,952,115 | A | 9/1999 | Hu et al. |
| 8,062,769 | B2 * | 11/2011 | Kai et al. ....................... 428/690 |
| 2004/0100190 | A1 * | 5/2004 | Kim et al. ..................... 313/504 |
| 2004/0137271 | A1 | 7/2004 | Sohn et al. |
| 2005/0084711 | A1 | 4/2005 | Sasaki et al. |
| 2009/0302742 | A1 | 12/2009 | Komori et al. |
| 2010/0187977 | A1 | 7/2010 | Kai et al. |

FOREIGN PATENT DOCUMENTS

| JP | 5-214333 A | 8/1993 |
| JP | 11-162650 A | 6/1999 |
| JP | 11-176578 A | 7/1999 |
| JP | 2003-31371 A | 1/2003 |
| JP | 2003-515897 T | 5/2003 |
| JP | 2004-79265 A | 3/2004 |
| JP | 2004-204234 A | 7/2004 |
| JP | 2005-93425 A1 | 4/2005 |
| JP | 2005-158691 A | 6/2005 |
| WO | WO 01/41512 A1 | 6/2001 |
| WO | WO 2007/063754 A1 | 6/2007 |
| WO | WO 2008/056746 A1 | 5/2008 |

OTHER PUBLICATIONS

Translation of the International Preliminary Report on Patentability dated Nov. 11, 2010 (PCT/IB/338 & PCT/IPEA/409).
English translation of Response Under Article 11 filed in PCT/JP2009/053713 dated Jan. 13, 2010.
International Search Report—dated Apr. 21, 2009 for PCT/JP2009/053713.

* cited by examiner

*Primary Examiner* — Andrew K Bohaty
(74) *Attorney, Agent, or Firm* — Birch Stewart Kolasch & Birch LLP

(57) ABSTRACT

Disclosed is an organic electroluminescent device (organic EL device) which can achieve high efficiency and long lifetime even when driven at low voltage. The organic El device comprises at least a light-emitting layer and an electron-transporting layer between an anode and a cathode facing each other. The electron-transporting layer consists of two layers, namely, a first electron-transporting layer and a second electron-transporting layer and the first electron-transporting layer and the second electron-transporting layer are arranged sequentially in this order from the light-emitting layer side to the cathode side. The first electron-transporting layer contains an indole derivative in which the ring nitrogen atom is substituted with an aromatic group and an aromatic ring is fused to the indole ring.

11 Claims, 1 Drawing Sheet

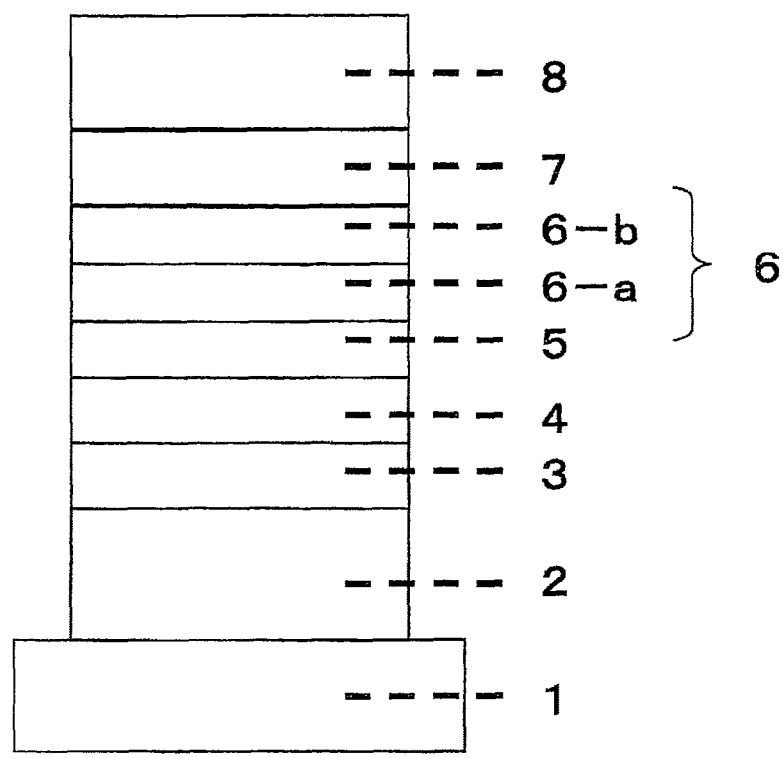

ORGANIC ELECTROLUMINESCENT DEVICE COMPRISING A FIRST ELECTRON-TRANSPORTING LAYER AND A SECOND ELECTRON-TRANSPORTING LAYER

FIELD OF TECHNOLOGY

This invention relates to an organic electroluminescent device (hereinafter referred to as organic EL device) and, more particularly, this invention relates to an organic EL device that can attain high efficiency and long lifetime even when driven at low voltage by using a compound of specified structure in the electron-transporting layer.

TECHNICAL BACKGROUND

An organic EL device in the simplest structure is generally constituted of a light-emitting layer and a pair of counter electrodes sandwiching the light-emitting layer and functions by utilizing the following phenomenon. Upon application of an electrical field between the electrodes, electrons are injected from the cathode and holes are injected from the anode and they recombine in the light-emitting layer; the energy level after the recombination returns from the conduction band to the valence band with release of energy in the form of light.

In recent years, organic thin films have been used in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting/electron-transporting layer composed of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been focused on commercial applications to high-performance flat panels featuring self-luminescence and high-speed response.

In another effort to enhance the luminous efficiency of the device, the use of phosphorescent materials in place of fluorescent materials is investigated. The aforementioned device comprising a hole-transporting layer composed of an aromatic diamine and a light-emitting layer composed of Alq3 and many other devices utilize fluorescence. The use of phosphorescence, that is, emission of light from the excited triplet state, is expected to enhance the luminous efficiency approximately three to four times that of the conventional devices utilizing fluorescence (emission of light from the excited singlet state). To achieve this objective, the use of coumarin derivatives and benzophenone derivatives in the light-emitting layer has been investigated, but these derivatives merely produced luminance at an extremely low level. Thereafter, europium complexes were tried in utilization of the excited triplet state, but they too failed to emit light at high efficiency. The studies on utilization of phosphorescence are mostly centered on the use of organic metal complexes such as the iridium complexes mentioned in patent document 1 as phosphorescent dopants.

Patent document 1: JP 2003-515897 A
Patent document 2: JP Hei 5-214333 A
Patent document 3: JP Hei 11-162650 A
Patent document 4: JP Hei 11-176578 A
Patent document 5: JP 2005-093425 A Further, studies are under way on enhancement of the efficiency and elongation of lifetime by means of lowering the driving voltage of the device. For example, patent document 2 discloses the use of quinolinol-based metal complexes such as Alq3. Even so, organic EL devices using such compounds require high driving voltage and show a short lifetime and there is a growing demand for electron-transporting materials capable of lowering the driving voltage, enhancing the efficiency, and elongating the lifetime still further.

Further, patent documents 3 and 4 disclose indolocarbazole compounds, but the disclosure is concerned with compounds in which the indolocarbazole skeleton is not linked to an aromatic heterocyclic group. Moreover, the documents recommend the disclosed indolocarbazole compounds for use as hole-transporting materials and commend them for their stability, but the documents do not teach at all the use of the disclosed indolocarbazole compounds as electron-transporting materials.

Further, patent document 5 discloses a scheme for improvement of the characteristics of the device by dividing an electron-transporting layer into a first electron-transporting layer and a second electron-transporting layer and using a specified compound in each layer. According to the disclosure, the intended effect can be manifested provided that the ionization potential of the first electron-transporting layer ($IP_1$) is related to the ionization potential of the second electron-transporting layer ($IP_2$) as $IP_1 < IP_2$.

DISCLOSURE OF THE INVENTION

Problems to be Solved by the Invention

In applications of organic EL devices to display devices such as flat panel displays, it is necessary to enhance the luminous efficiency of the device and, at the same time, to fully secure the driving stability of the device. Under the aforementioned circumstances, an object of this invention is to provide an organic EL device that performs at high efficiency with good driving stability even at low voltage and is suitable for practical use.

Means to Solve the Problems

Accordingly, this invention relates to an organic electroluminescent device comprising at least a light-emitting layer and an electron-transporting layer disposed between an anode and a cathode facing each other wherein the electron-transporting layer consists of two layers, namely, a first electron-transporting layer and a second electron-transporting layer, the first electron-transporting layer and the second electron-transporting layer are arranged sequentially in this order from the light-emitting layer side to the cathode side, and the first electron-transporting layer contains a compound represented by the following general formula (1).

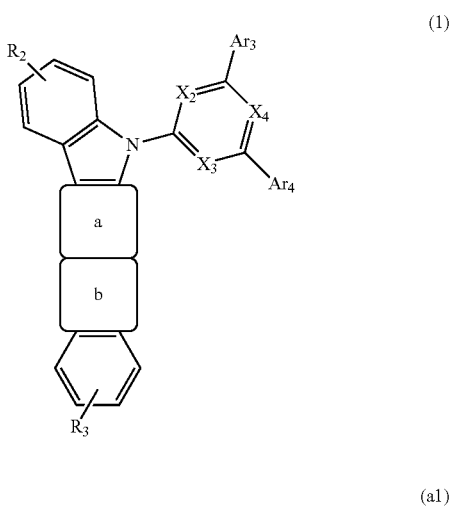

(1)

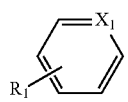

(a1)

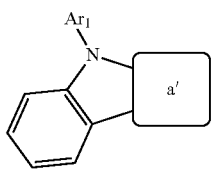

(a2)

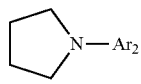

(b1)

In general formula (1), ring a is an aromatic or heterocyclic ring fused to two adjacent rings and represented by formula (a1) or (a2), ring a' is an aromatic or heterocyclic ring fused to three adjacent rings and is represented by formula (a1), $X_1$ is CH or N, and ring b is a heterocyclic ring fused to two adjacent rings and represented by formula (b1); $Ar_1$ to $Ar_4$ each is independently a substituted or unsubstituted aromatic hydrocarbon group or a substituted or unsubstituted aromatic heterocyclic group; $R_1$ to $R_3$ each is independently a hydrogen atom, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group; $X_2$, $X_3$, and $X_4$ each is independently CH or N and at least one of them is N.

Of the compounds represented by the aforementioned general formula (1), those which are represented by the following general formula (2) are preferred:

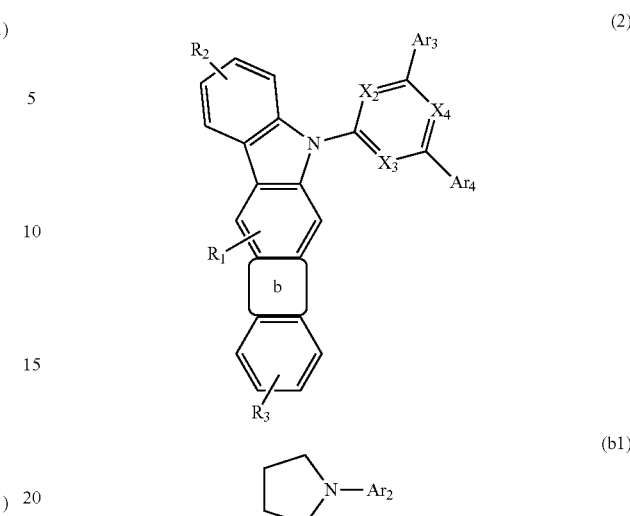

(2)

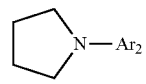

(b1)

wherein ring b, $Ar_2$ to $Ar_4$, $R_1$ to $R_3$, and $X_2$ to $X_4$ respectively have the same meaning as ring b, $Ar_2$ to $Ar_4$, $R_1$ to $R_3$, and $X_2$ to $X_4$ in general formula (1).

In the aforementioned general formula (1) or (2), $X_2$ to $X_4$ each is CH or N and $X_2$ to $X_4$ preferably satisfy one of the following conditions: 1) one of $X_2$ to $X_4$ is a nitrogen atom; 2) $X_4$ is a nitrogen atom; 3) two of $X_2$ to $X_4$ are nitrogen atoms; 4) $X_2$ and $X_3$ are nitrogen atoms; and 5) $X_2$ to $X_4$ are all nitrogen atoms.

In the aforementioned general formula (1) or (2), $Ar_1$ to $Ar_4$ each is independently a substituted or unsubstituted aromatic hydrocarbon group or a substituted or unsubstituted aromatic heterocyclic group, preferably, a substituted or unsubstituted aromatic hydrocarbon group of 5-10 carbon atoms or a substituted or unsubstituted aromatic heterocyclic group of 2-5 carbon atoms.

In the aforementioned general formula (1) or (2), $R_1$ to $R_3$ each is independently a hydrogen atom, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group and, of these groups, a hydrogen atom, a substituted or unsubstituted aromatic hydrocarbon group of 5-18 carbon atoms, and a substituted or unsubstituted aromatic heterocyclic group of 3-17 carbon atoms are preferred.

Further, this invention relates to an organic electroluminescent device whose second electron-transporting layer comprises a quinolinol-based metal complex.

BRIEF DESCRIPTION OF THE DRAWING

FIG. 1 schematically shows the cross section of an example of an organic EL device to be provided by this invention.

BEST MODE FOR CARRYING OUT THE INVENTION

In the organic electroluminescent device of this invention comprising at least a light-emitting layer and an electron-transporting layer between an anode and a cathode facing each other, the electron-transporting layer consists of two layers, that is, a first electron-transporting layer and a second electron-transporting layer, the first electron-transporting layer and the second electron-transporting layer are arranged sequentially in this order from the light-emitting layer side to the cathode side, and the first electron-transporting layer contains a compound represented by the aforementioned general formula (1). A compound represented by the aforementioned general formula (1) or (2) will be hereinafter referred to also as a compound of general formula (1) or (2).

The aforementioned general formula (1) is understood to be wider in meaning than general formula (2) and include general formula (2). Thus, it is seen that ring a in general formula (1) becomes an aromatic ring represented by formula (a1) wherein $X_1$ is CH and R is H in general formula (2). That is, there is a difference between general formula (1) and general formula (2) in that the ring a in the former becomes a benzene ring in the latter. In general formulas (1) and (2), the same symbol has the same meaning. Any subject common to general formulas (1) and (2) may be explained in the section dealing with general formula (1) and the same will hold for any compound common to general formulas (1) and (2).

In the aforementioned general formula (1), ring a is an aromatic or heterocyclic ring fused to two adjacent rings and represented by formula (a1) or (a2). In formula (a2), ring a' is an aromatic or heterocyclic ring fused to three adjacent rings and represented by formula (a1) and rings other than ring a' in formula (a2) are never fused to other rings in general formula (1). In the aforementioned general formulas (1) and (2), ring b is a heterocyclic ring fused to two adjacent rings and represented by general formula (b1).

In the aforementioned general formulas (1) and (2), $X_1$, $X_2$, $X_3$, and $X_4$ each is independently CH or N and at least one of $X_2$, $X_3$, and $X_4$ is N. Although at least one of $X_2$, $X_3$, and $X_4$ is N, one, two, or three of them are preferably Ns; in the case where one of them is N, it is preferably $X_4$; in the case where two of them are Ns, they are preferably $X_2$ and $X_3$.

The groups $Ar_1$ to $Ar_4$ are aromatic hydrocarbon groups or aromatic heterocyclic groups and they may be substituted or unsubstituted.

Examples of the unsubstituted aromatic hydrocarbon groups include benzene, naphthalene, anthracene, and phenanthrene. Aromatic hydrocarbon groups of 5-10 carbon atoms are preferred and benzene is more preferred.

Examples of the unsubstituted aromatic heterocyclic groups include thiophene, furan, pyran, pyrrole, imidazole, pyrazole, isothiazole, isoxazole, pyridine, pyrazine, pyrimidine, pyridazine, frazan, thiazole, oxazole, triazole, and carbazole. Aromatic heterocyclic groups of 2-5 carbon atoms are preferred and nitrogen-containing six-membered aromatic heterocyclic groups such as pyridine, pyrimidine, and triazine are more preferred.

In the case where the aforementioned aromatic hydrocarbon groups or aromatic heterocyclic groups contain substituents, examples of such substituents include an alkyl group, an aralkyl group, an alkenyl group, an alkynyl group, a cyano group, a dialkylamino group, a diarylamino group, a dialkylamino group, an amino group, a nitro group, an acyl group, an alkoxycarbonyl group, a carboxyl group, an alkoxyl group, an alkylsulfonyl group, a haloalkyl group, a hydroxyl group, an amide group, an aromatic hydrocarbon group, and an aromatic heterocyclic group. An alkyl group of 1-10 carbon atoms, an aralkyl group of 4-15 carbon atoms, an alkoxyl group of 1-15 carbon atoms, an amino group, an aromatic hydrocarbon group of 5-18 carbon atoms, and an aromatic heterocyclic group of 3-17 carbon atoms are preferred. The aralkyl group as used in this specification includes a heteroaralkyl group. The aromatic hydrocarbon groups or aromatic heterocyclic groups may contain the aforementioned substituents and, in such a case, the number of carbon atoms is computed by counting in the number of carbon atoms in the substituents. In the case where the aforementioned substituents can contain an infinite number of carbon atoms such as alkyl groups and aryl groups, the number of carbon atoms is preferably 20 or less.

In general formulas (1) and (2), $R_1$ to $R_3$ each is a hydrogen atom, an alkyl group, an aralkyl group, an alkenyl group, an alkynyl group, a cyano group, a dialkylamino group, a diarylamino group, a dialkylamino group, an amino group, a nitro group, an acyl group, an alkoxycarbonyl group, a carboxyl group, an alkoxyl group, an alkylsulfonyl group, a haloalkyl group, a hydroxyl group, an amide group, an aromatic hydrocarbon group, or an aromatic heterocyclic group. An alkyl group of 1-10 carbon atoms, an aralkyl group of 4-15 carbon atoms, an alkoxyl group of 1-15 carbon atoms, an amino group, an aromatic hydrocarbon group of 5-18 carbon atoms, and an aromatic heterocyclic group of 4-17 carbon atoms are preferred and an aromatic hydrocarbon group of 5-18 carbon atoms and an aromatic heterocyclic group of 3-17 carbon atoms are more preferred. The aforementioned aromatic hydrocarbon groups or aromatic heterocyclic groups may contain substituents and, in such a case, the number of carbon atoms is computed by counting in the number of carbon atoms in the substituents. In the case where the aforementioned $R_1$ to $R_3$ are groups which can contain an infinite number of carbon atoms such as alkyl groups and aryl groups, the number of carbon atoms is preferably 20 or less.

The first electron-transporting layer may be constituted of a compound selected from those compounds which are represented by general formula (1), advantageously from those compounds which are represented by general formula (2), or it may be constituted of a mixture of two or more compounds.

The compounds represented by general formula (1) or (2) can be produced readily by any of known methods, for example, by a method which involves the following sequence of reactions and is based on the synthetic examples reported in Tetrahedron, 1991, Vol. 47, No. 37, pp. 7739-7750 and Archiv der Pharmazie (Weinheim, Germany), 1987, 320 (3), pp. 280-282.

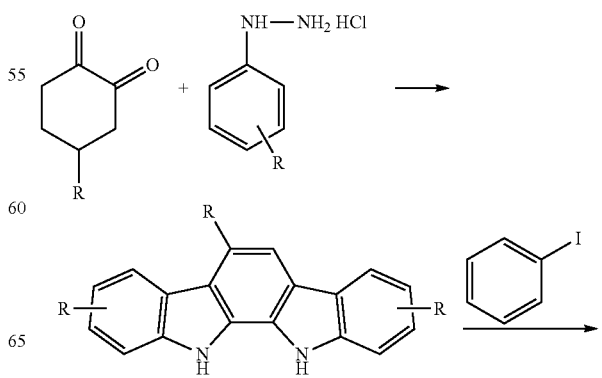

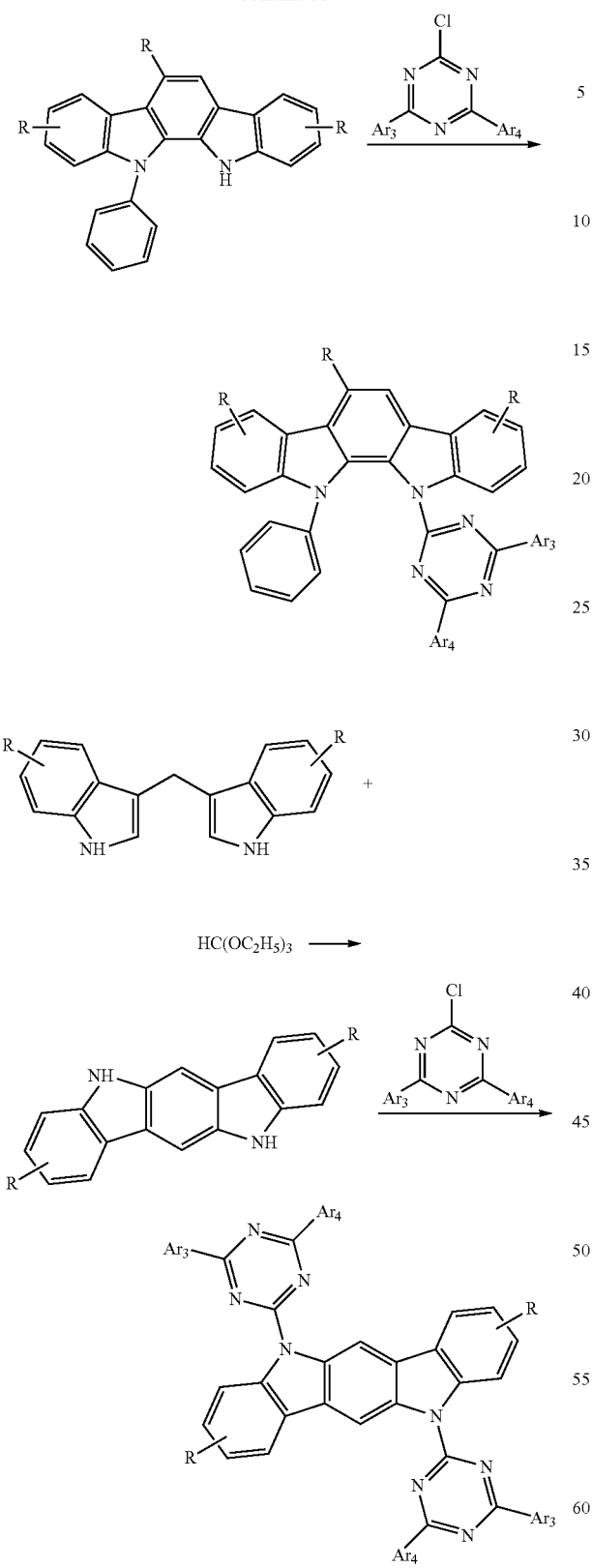
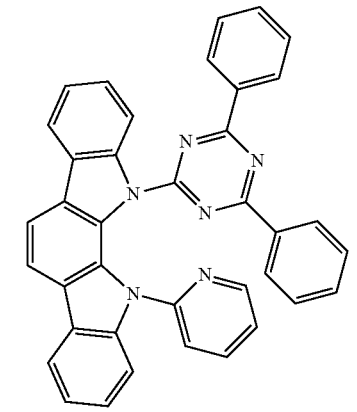
A-1
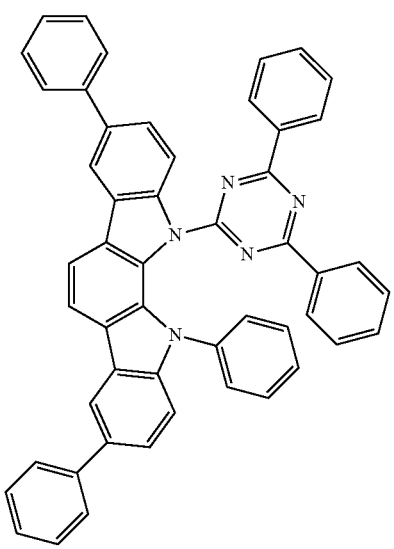
A-2
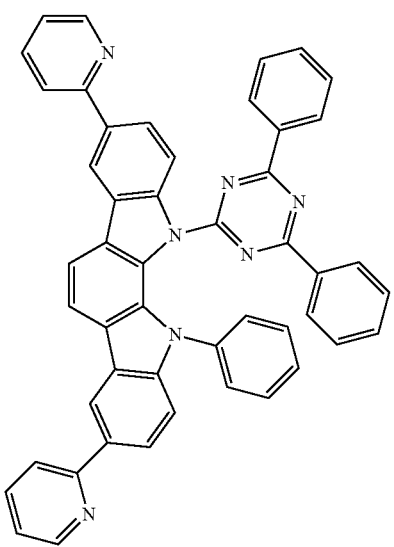
A-3
Preferable examples of the compounds represented by the aforementioned general formulas (1) and (2) are shown below, but are not limited thereto.

A-4
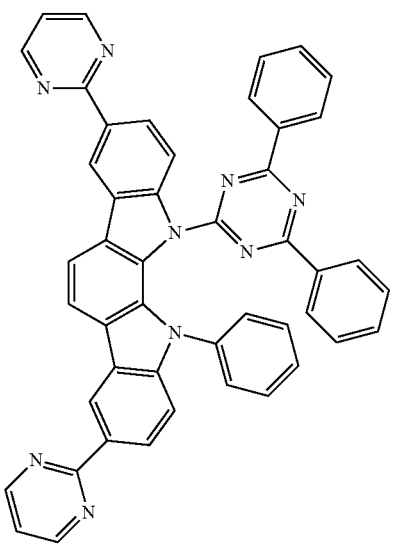
A-5
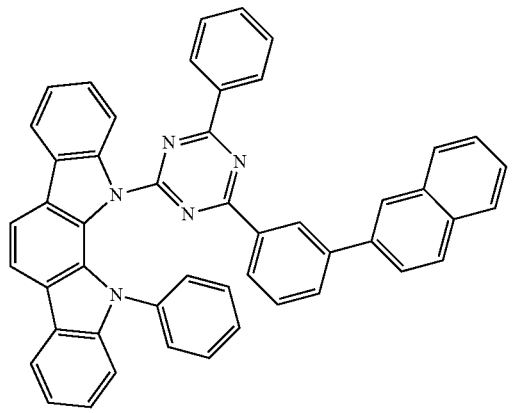
A-6
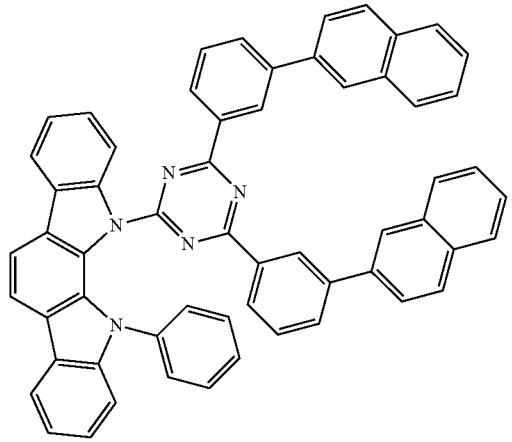
A-7
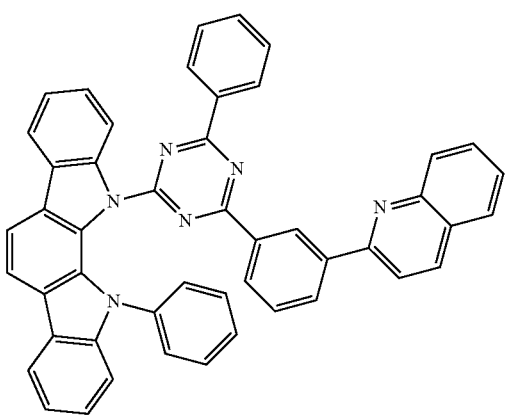
A-8
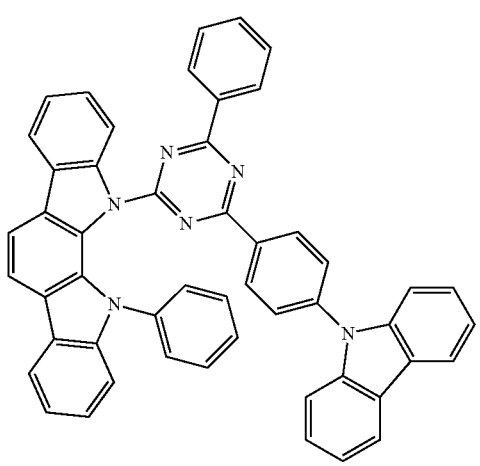
A-9
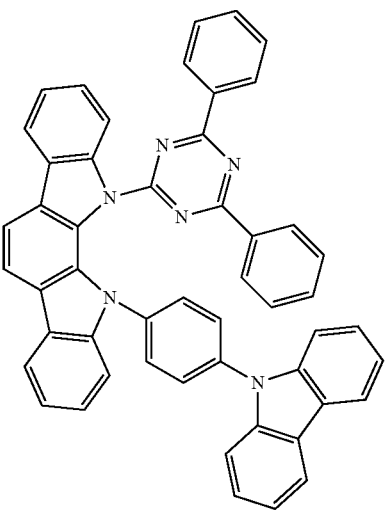

A-10
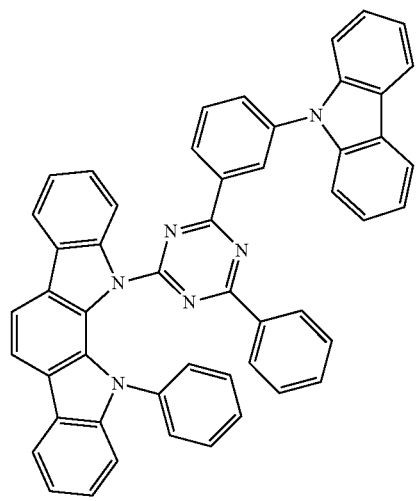
A-11
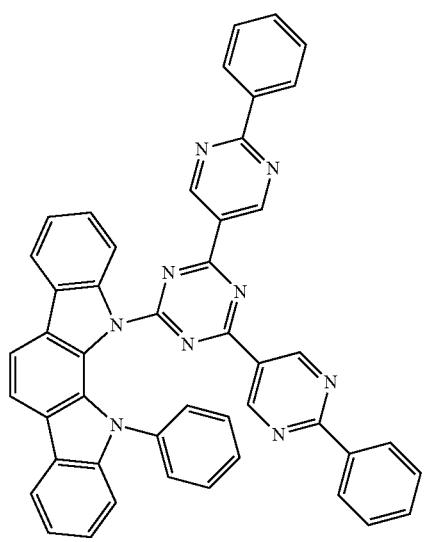
A-12
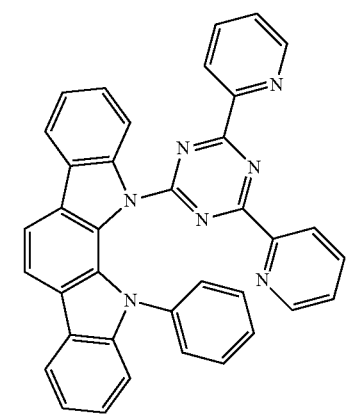
A-13
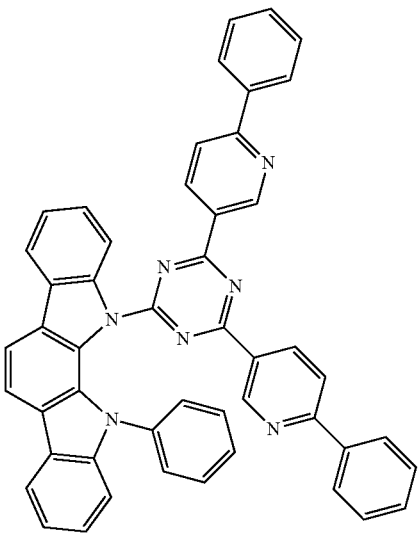
A-14
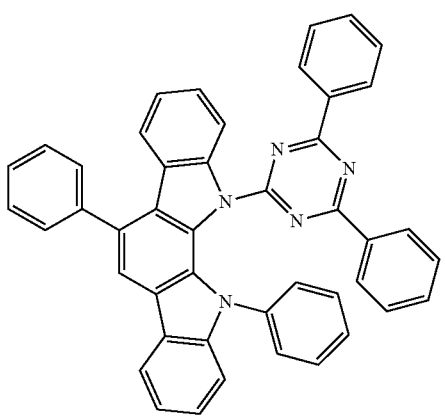
A-15
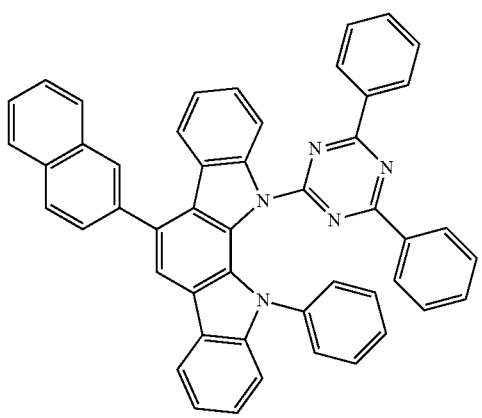

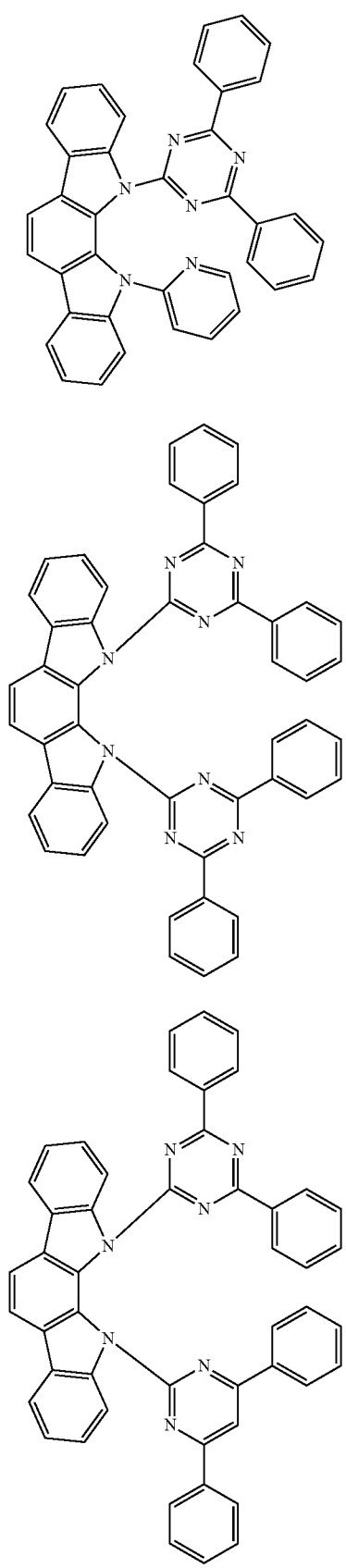
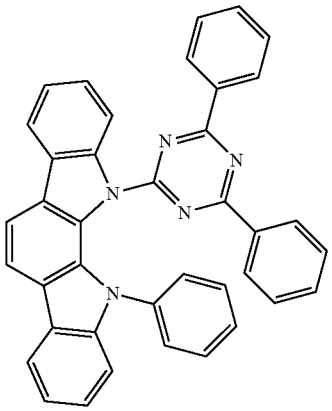
A-16
A-17
A-18
A-19
A-20
A-21
A-22

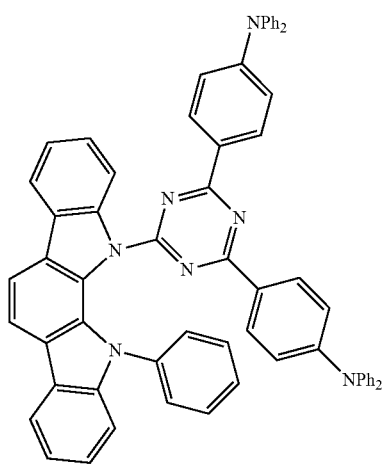
A-23
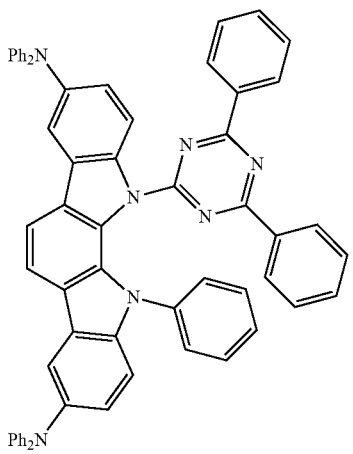
A-26
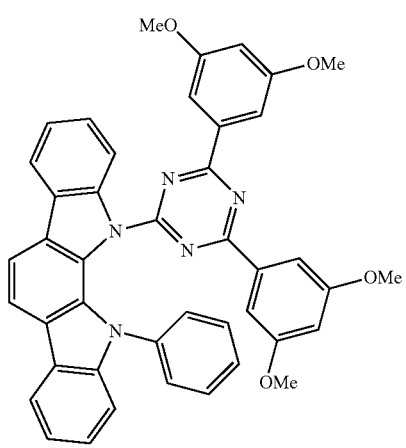
A-24
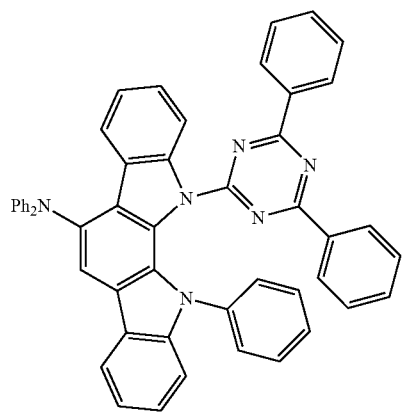
A-27
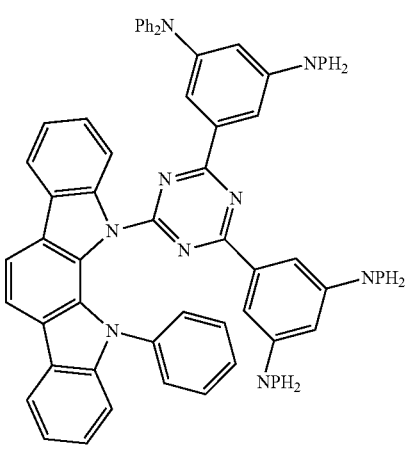
A-25
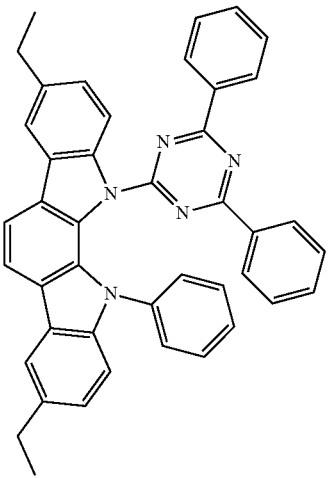
A-28

A-29
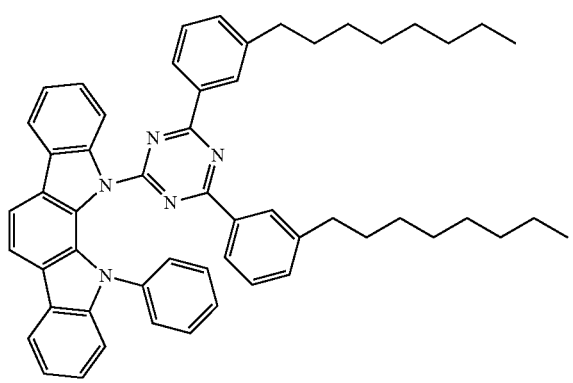
A-30
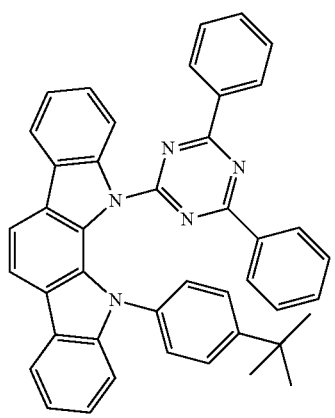
A-31
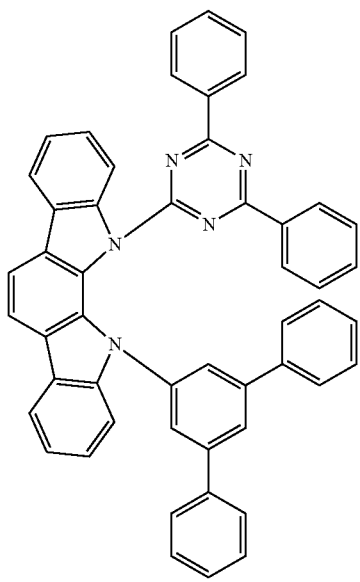
A-32
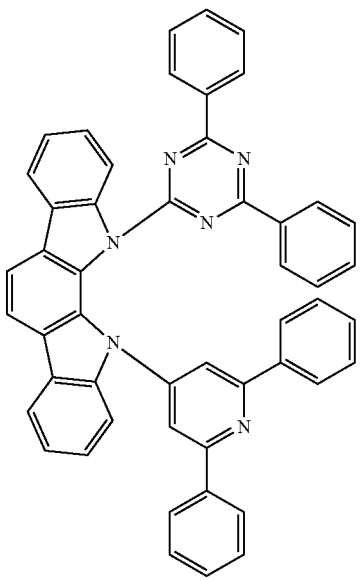
B-1
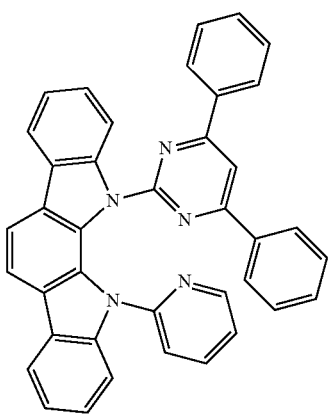
B-2
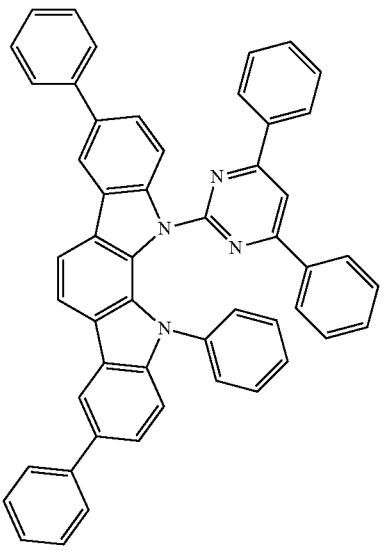

B-3
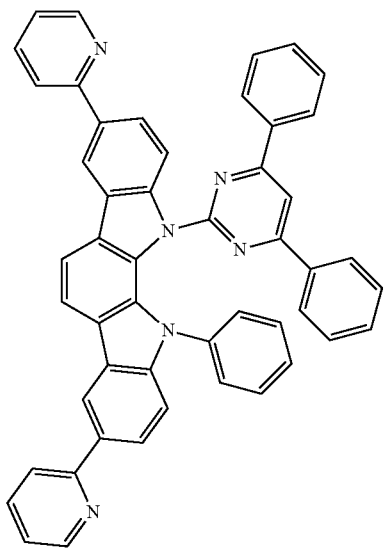
B-4
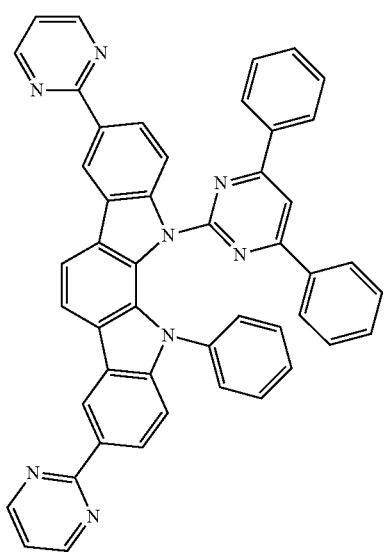
B-5
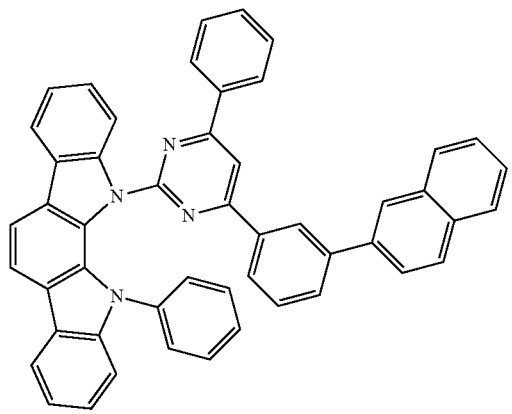
B-6
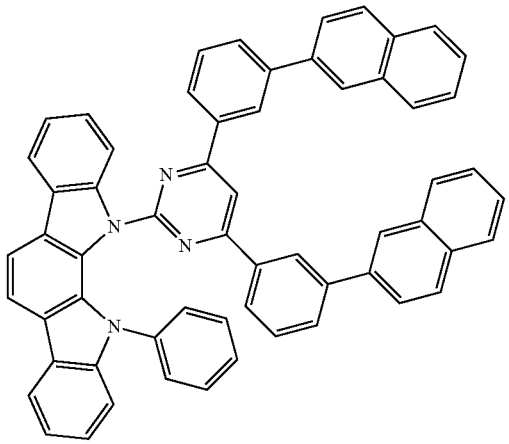
B-7
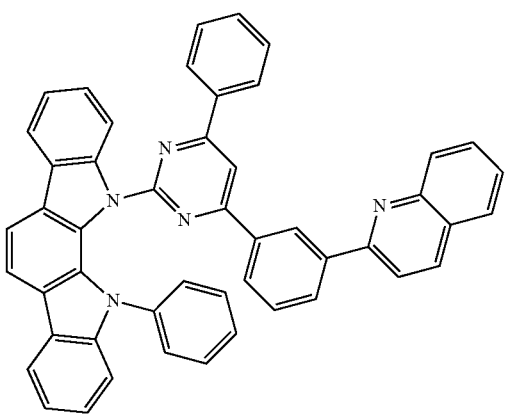
B-8
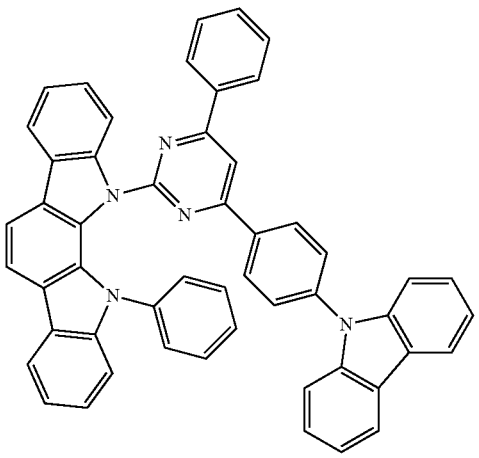

B-9
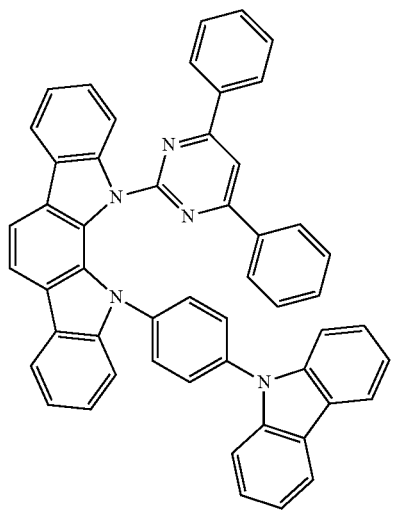
B-10
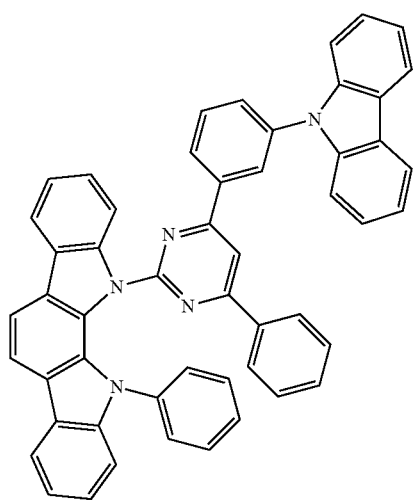
B-11
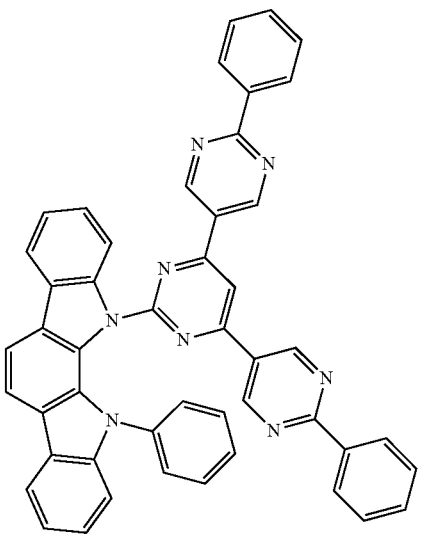
B-12
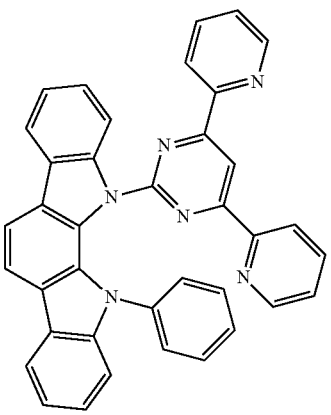
B-13
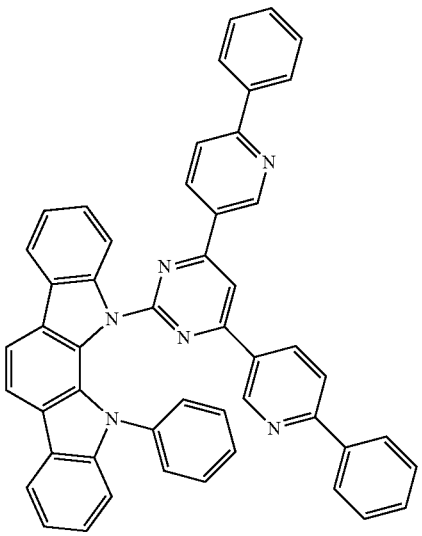
B-14
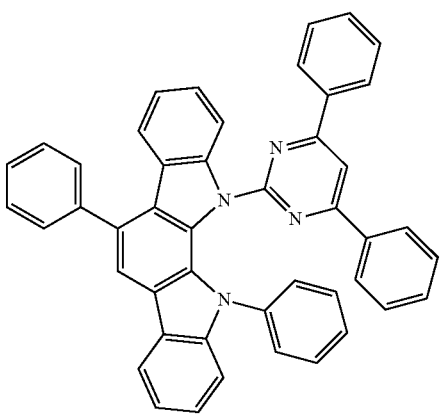

B-15
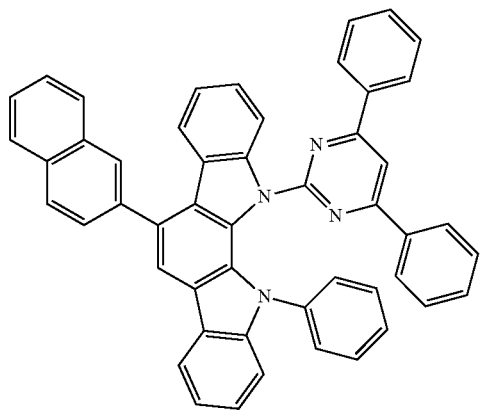
B-16
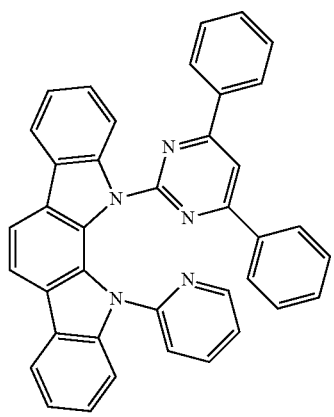
B-17
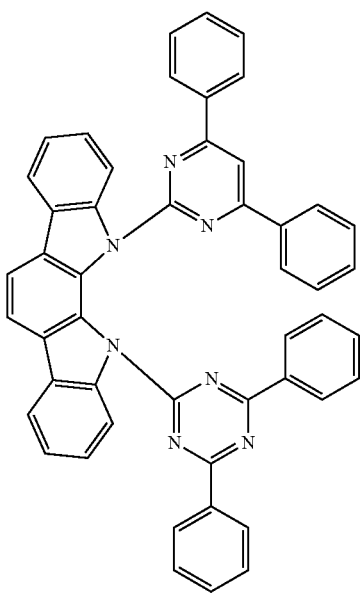
B-18
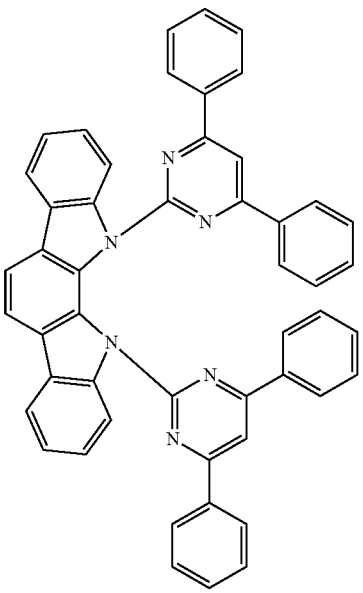
B-19
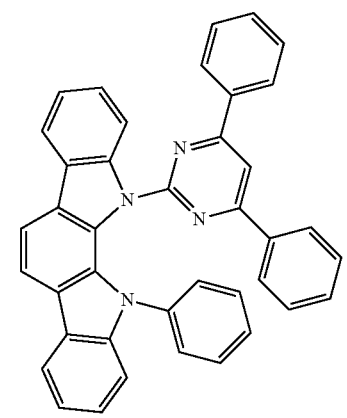
B-20
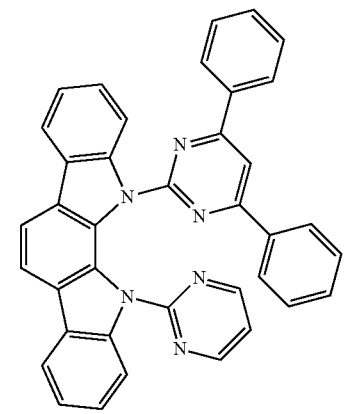

B-21
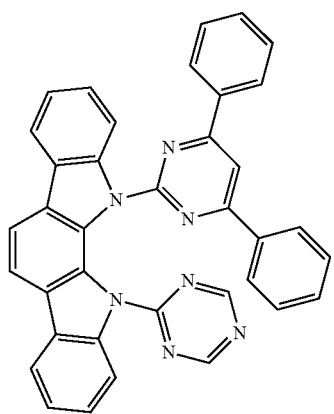
B-22
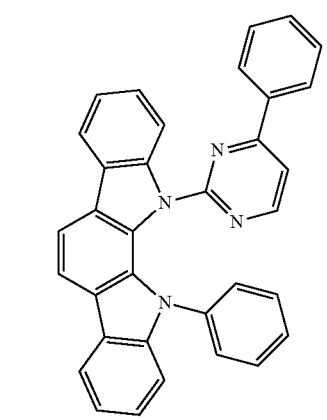
B-23
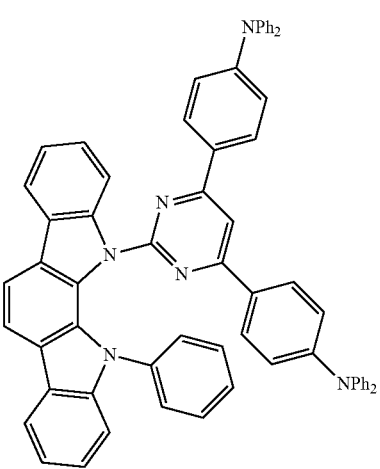
B-24
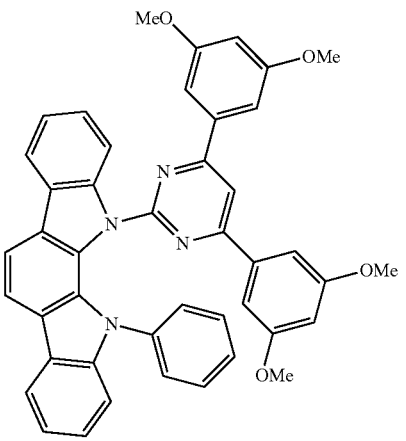
B-25
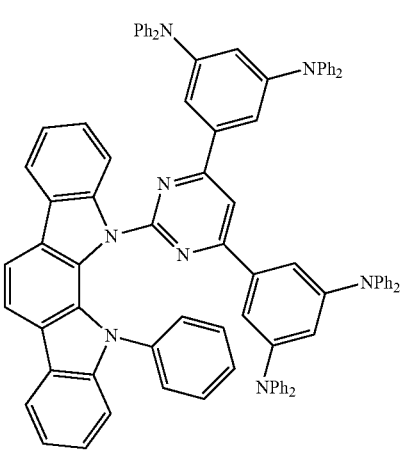
B-26
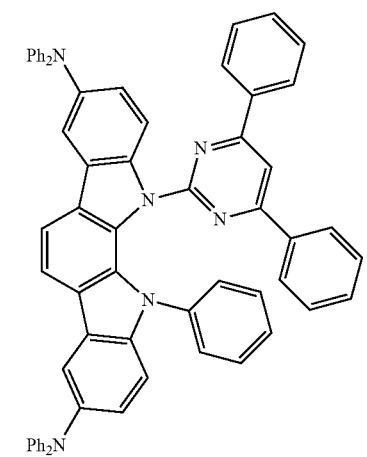

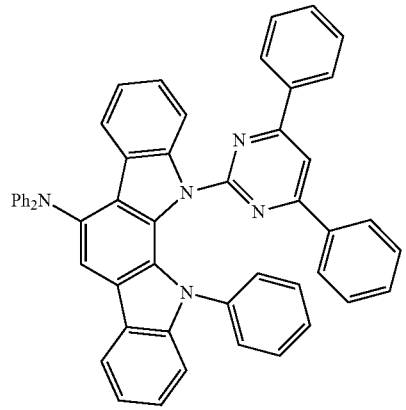
B-27
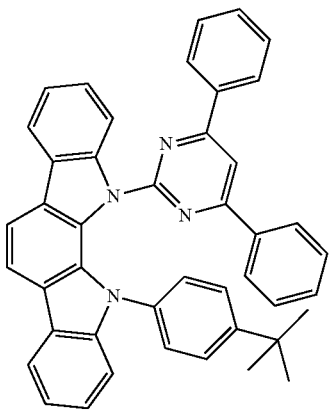
B-30
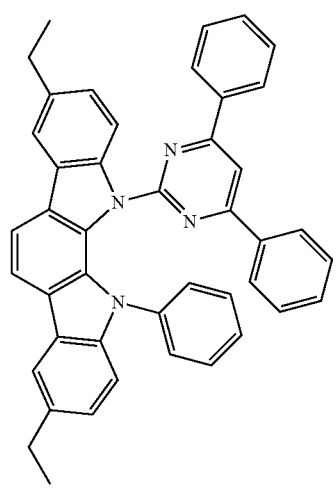
B-28
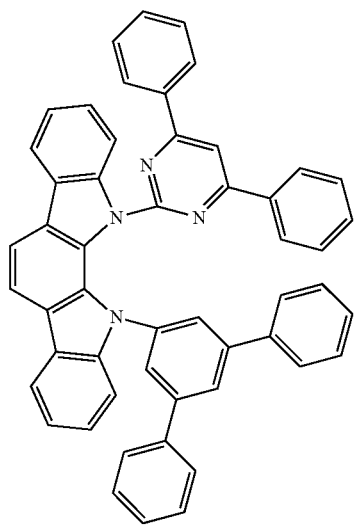
B-31
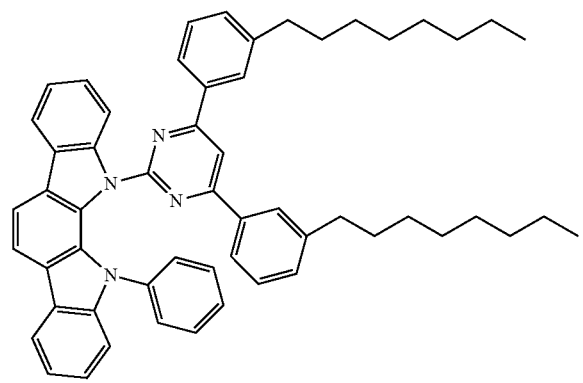
B-29
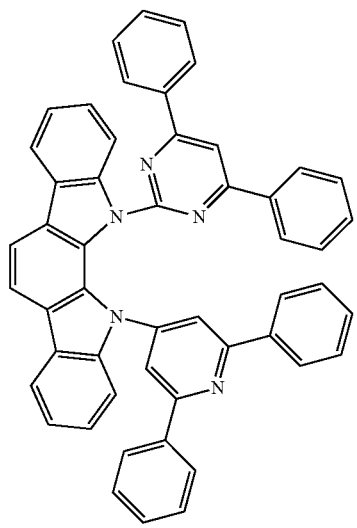
B-32

C-1
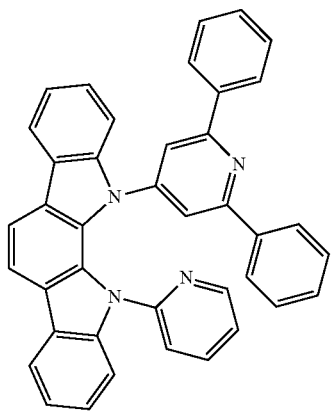
C-2
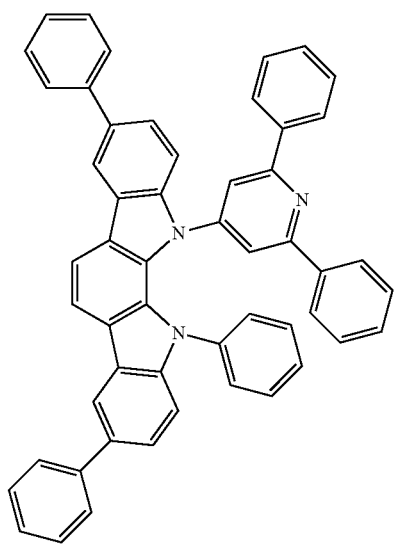
C-3
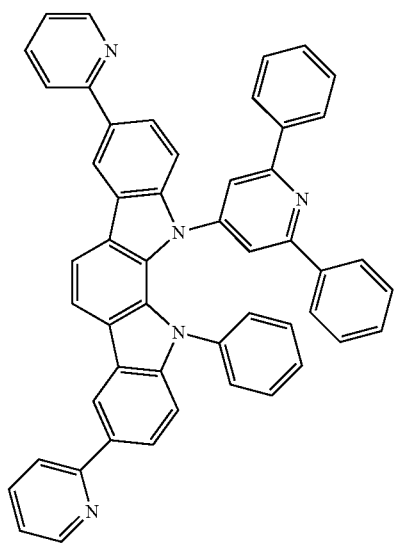
C-4
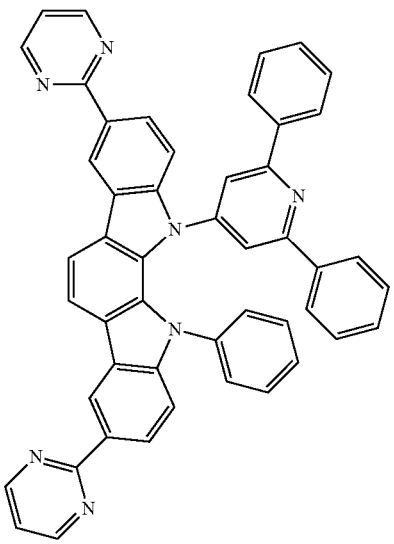
C-5
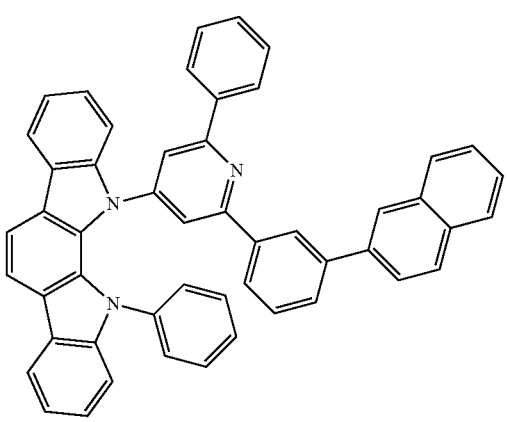
C-6
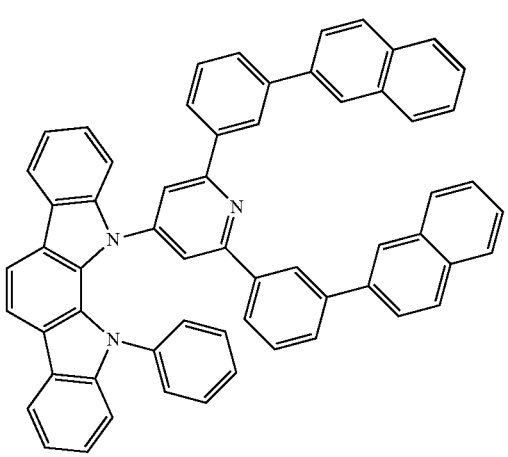

C-7
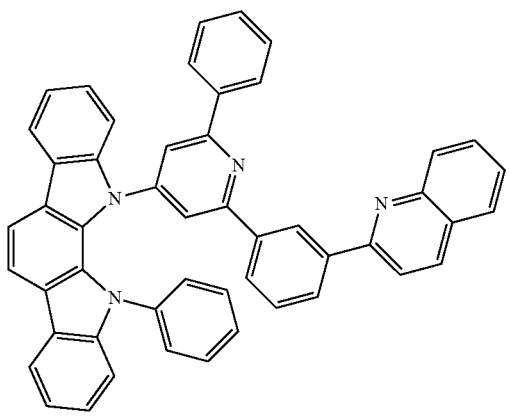
C-8
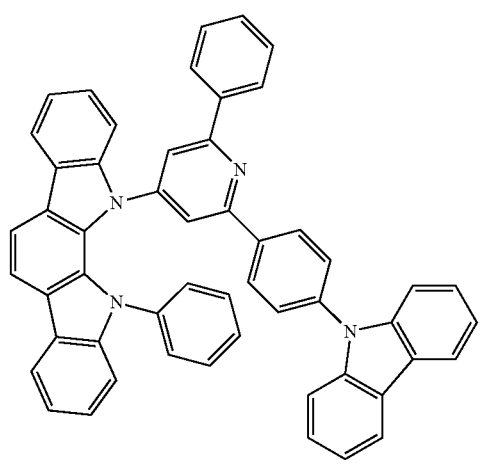
C-9
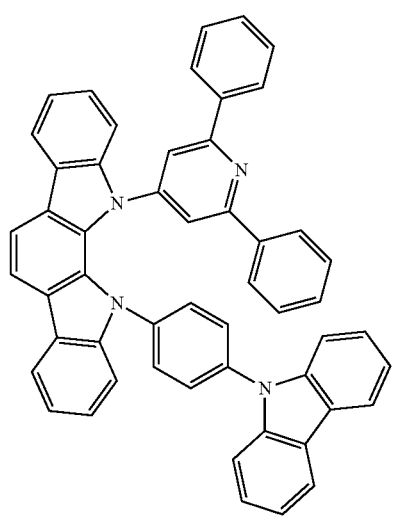
C-10
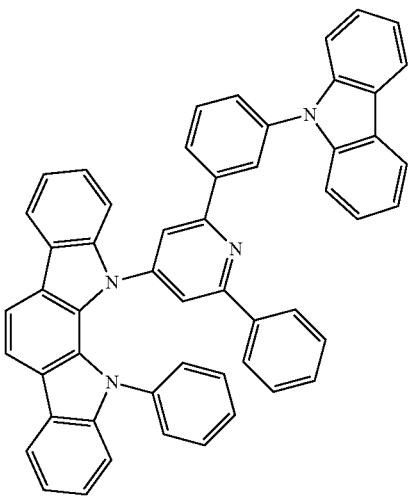
C-11
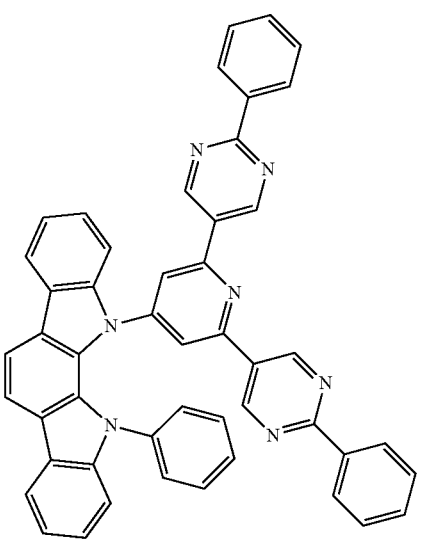
C-12
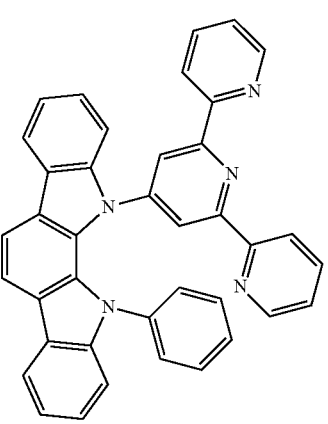

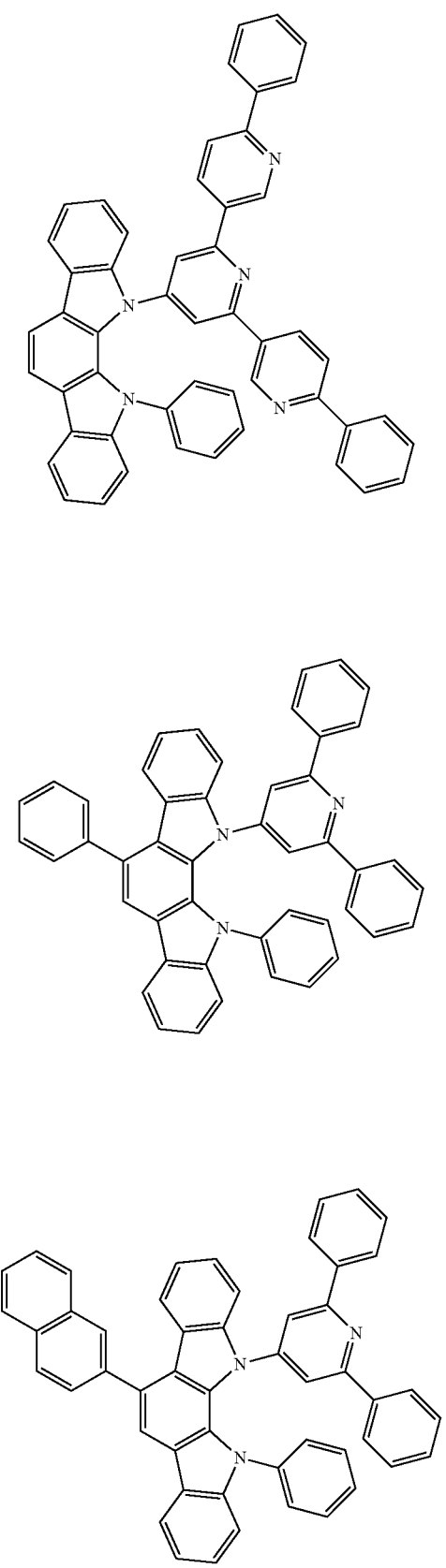
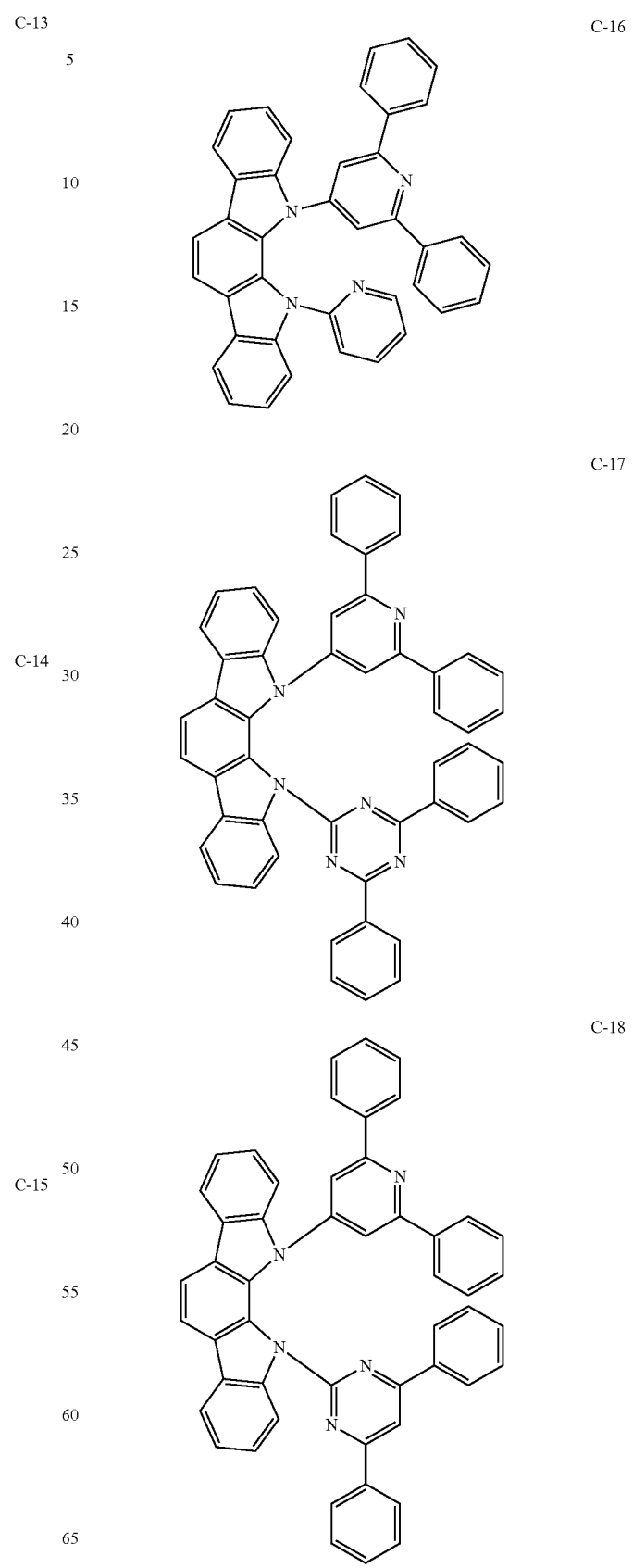

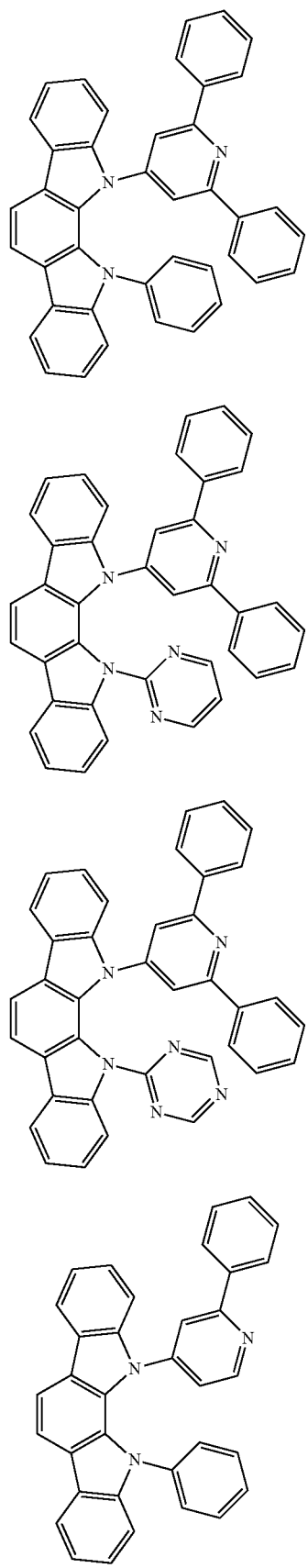
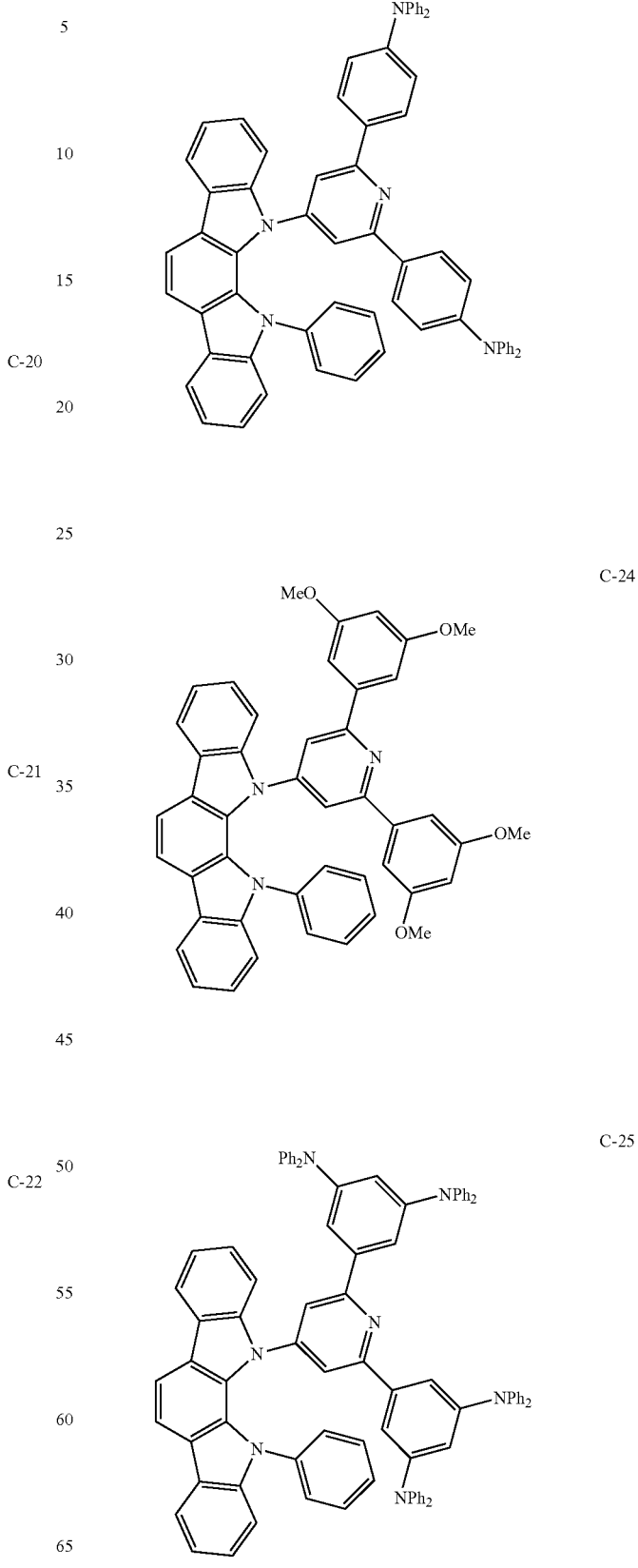

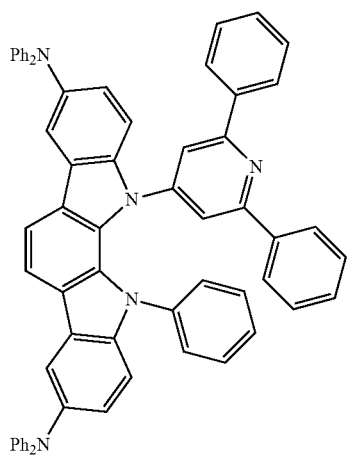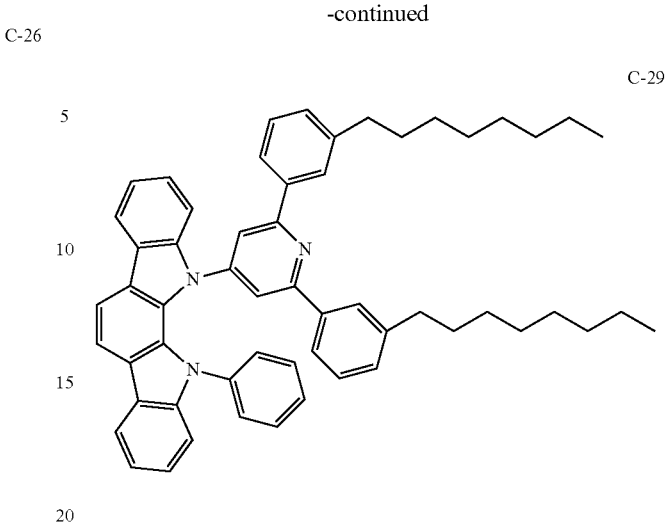

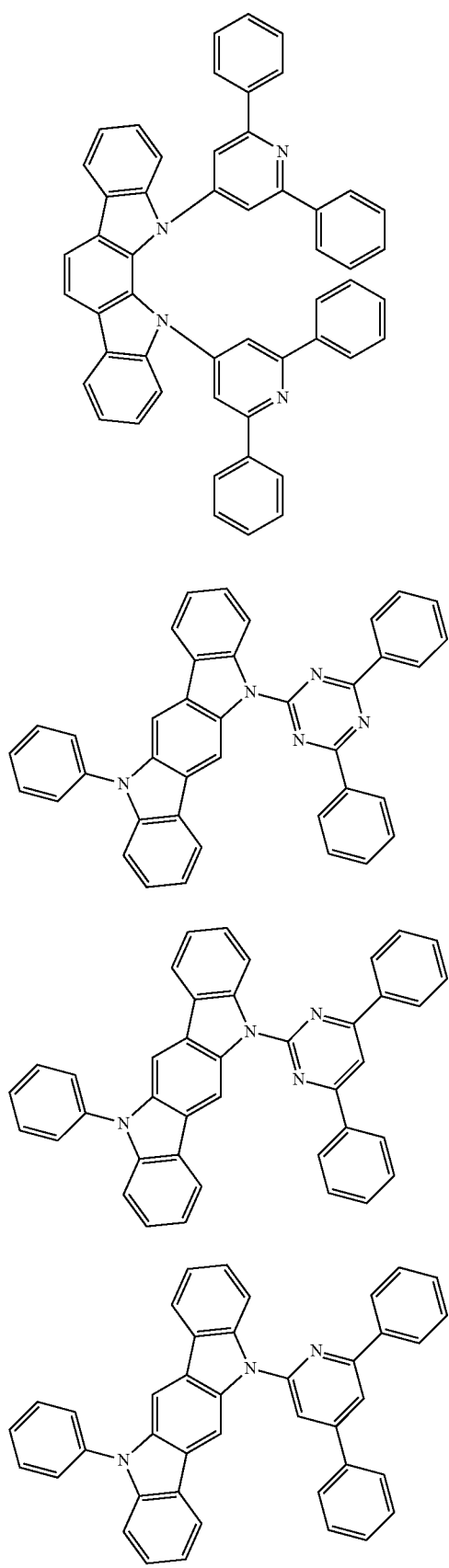
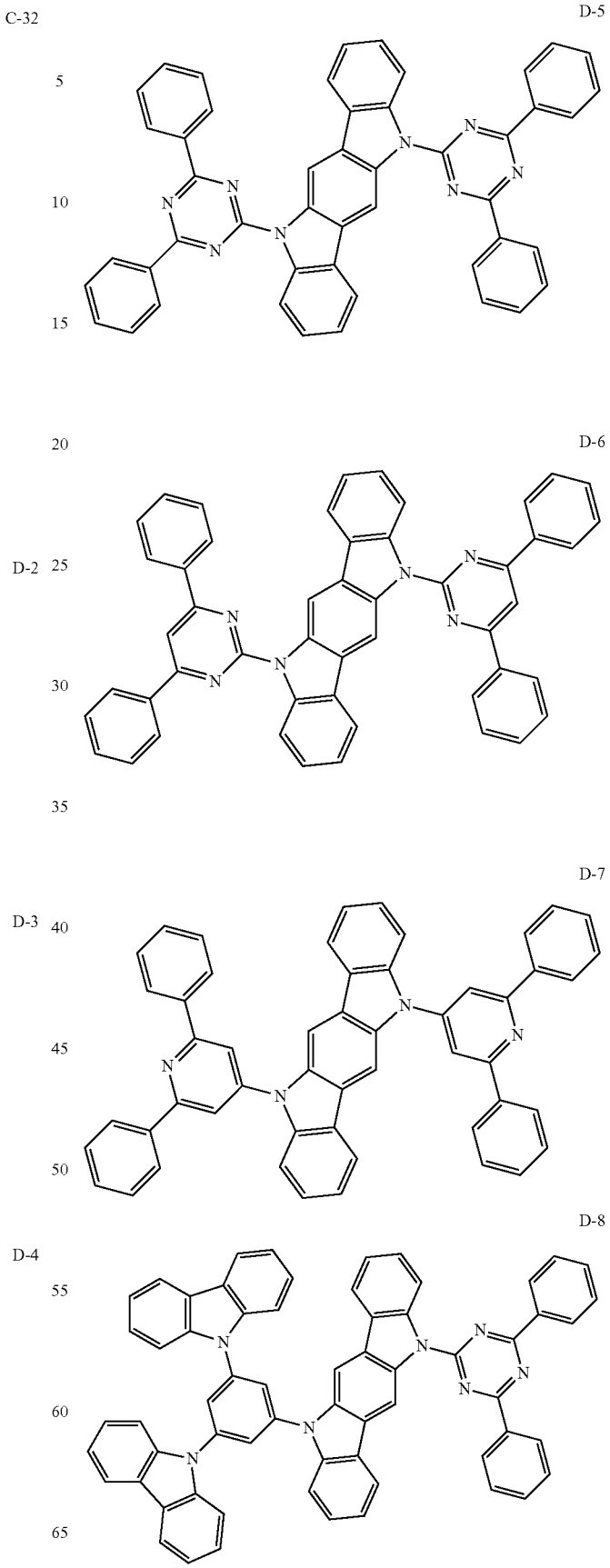

D-9
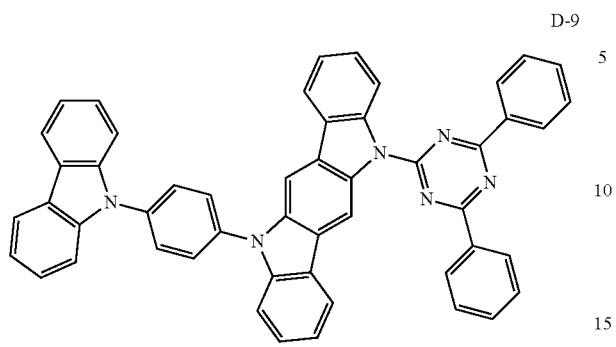
E-1
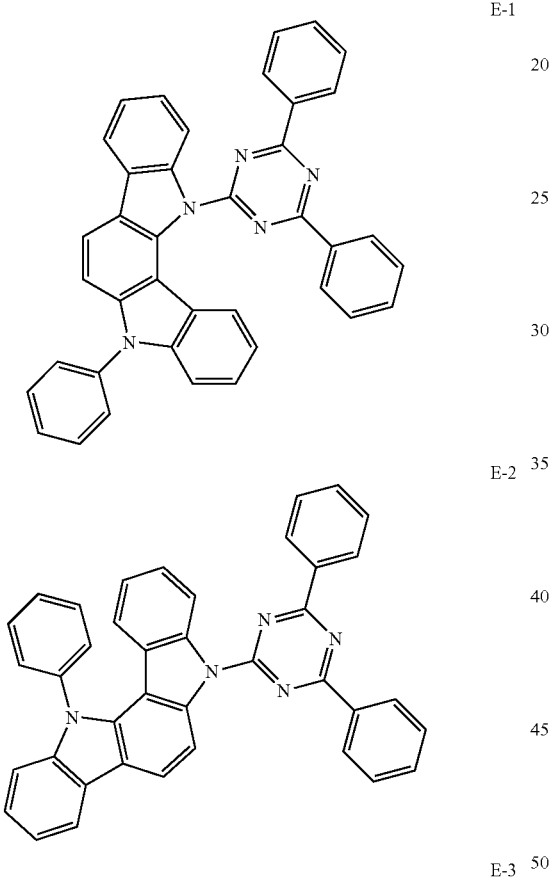
E-2
E-3
E-4
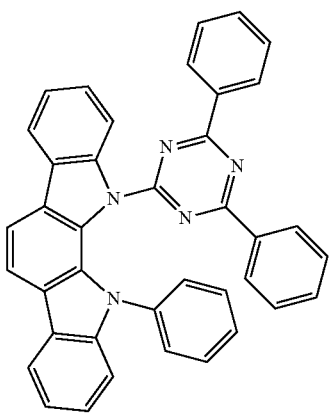
E-5
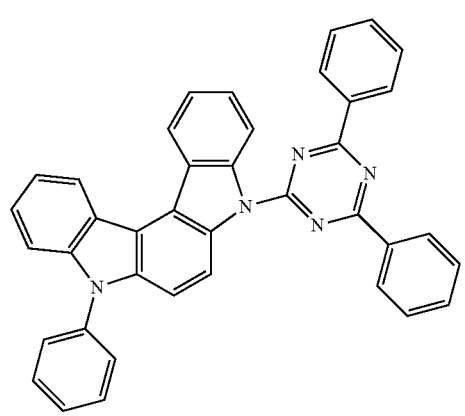
E-6
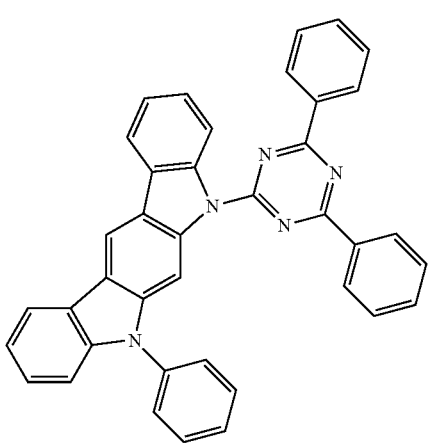

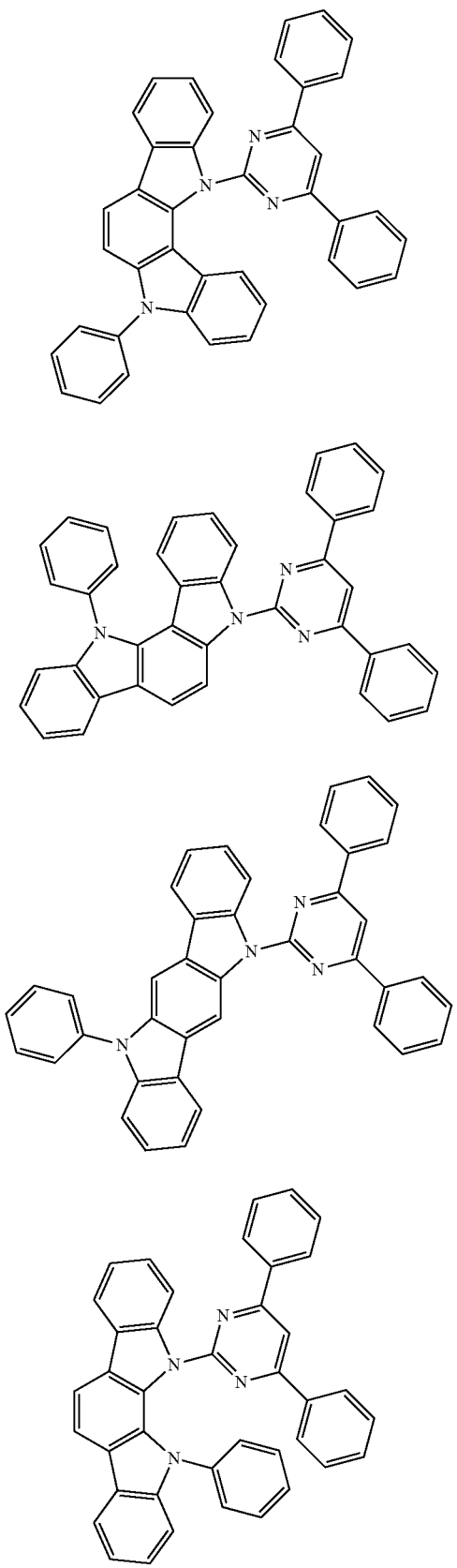
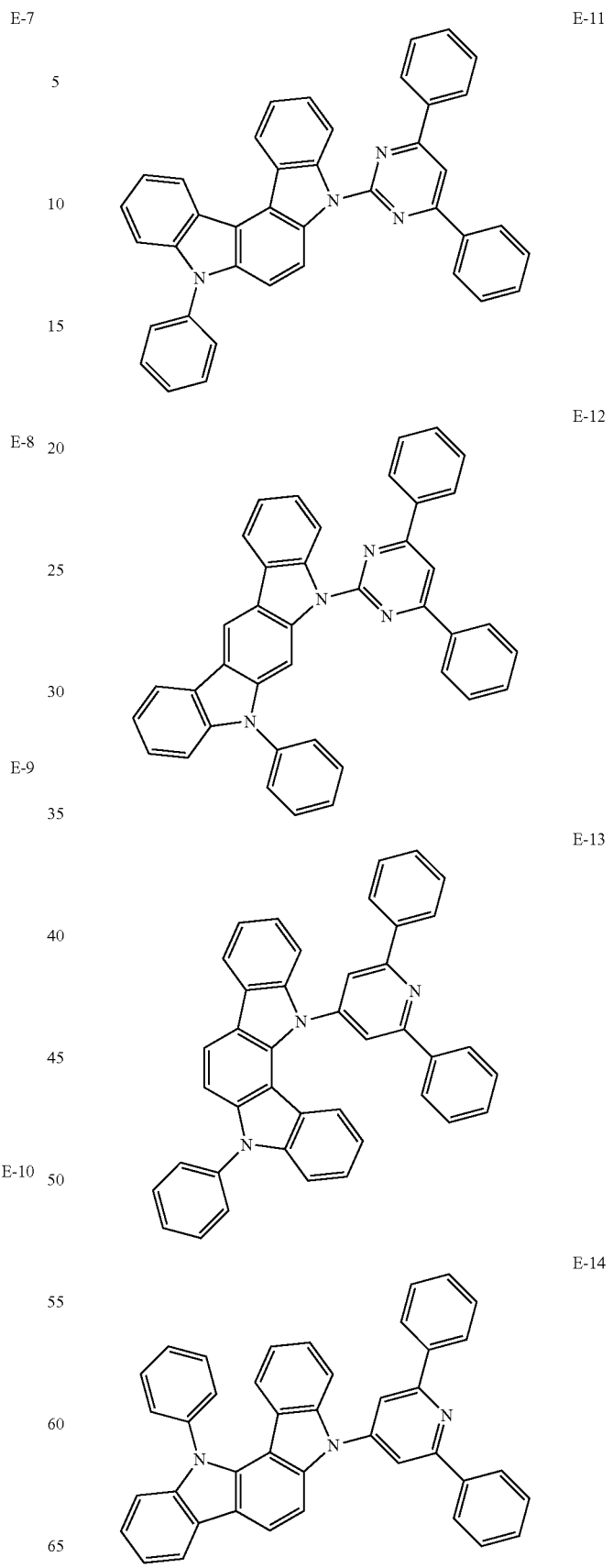

E-15
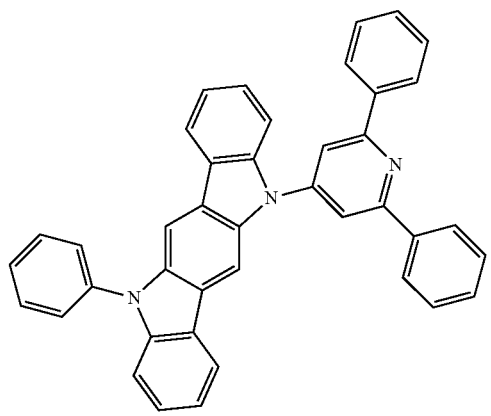
E-16
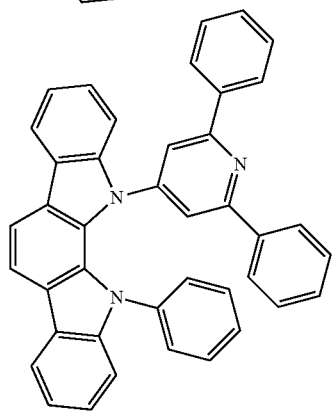
E-17
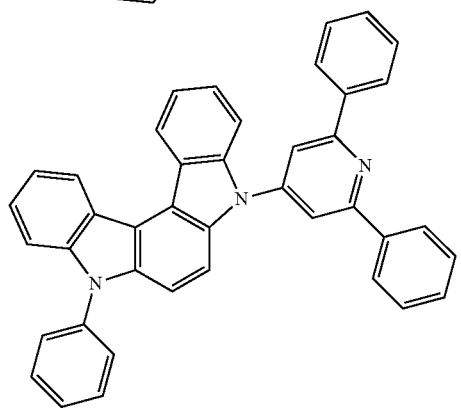
E-18
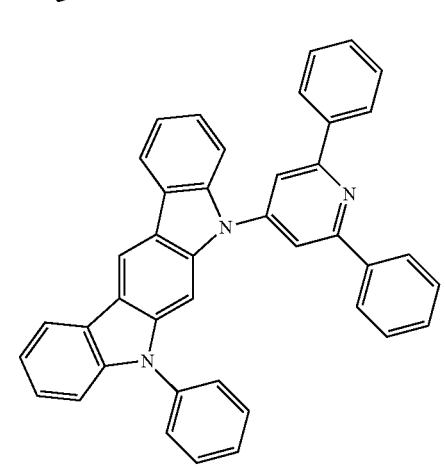
G-1
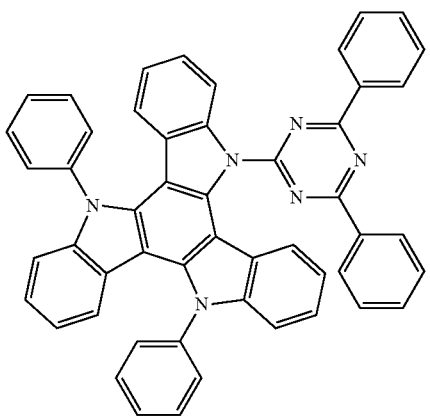
G-2
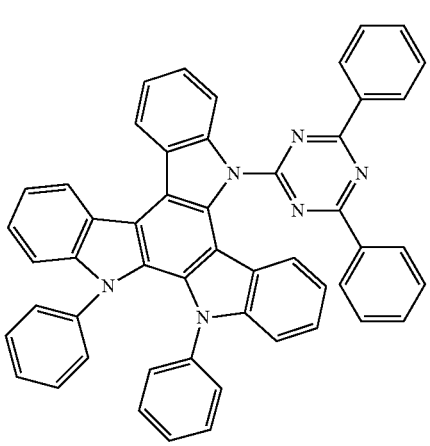
G-3
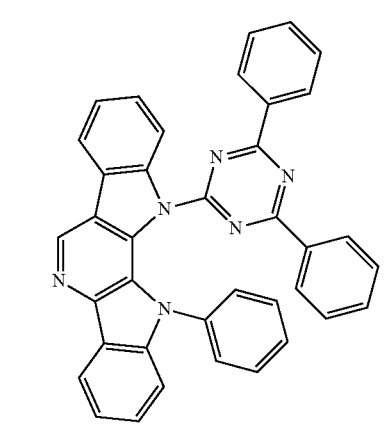
G-4
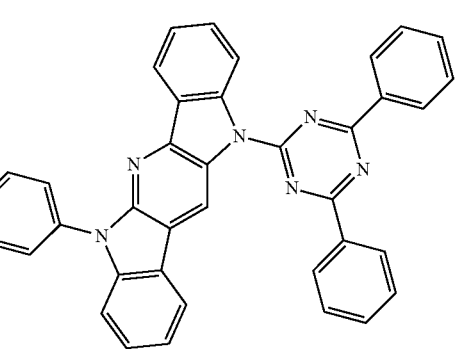

-continued

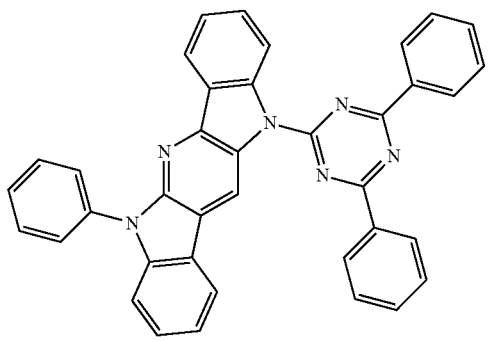

G-5

In the organic EL device of this invention, the second electron-transporting layer is preferably made from an electron-transporting material which can inject electrons from the cathode smoothly and any material in general use for this purpose may be used. Substituted or unsubstituted quinolinol-based metal complexes, typically Alq3 (aluminum quinolinol complex) and Liq (lithium quinolinol complex) are preferred. Moreover, the ionization potential of the first electron-transporting layer ($IP_1$) and the ionization potential of the second electron-transporting layer ($IP_2$) need not satisfy the relationship $IP_1 < IP_2$; rather, better results may sometimes be obtained when the relationship $IP_2 < IP_1$ is satisfied.

The structure of an organic EL device to be provided by this invention will be explained with reference to the drawing, but will not be limited to the one illustrated.

Explanation of symbols: 1 substrate; 2 anode; 3 hole-injecting layer; 4 hole-transporting layer; 5 light-emitting layer; 6 electron-transporting layer; 7 electron-injecting layer; 8 cathode.

(1) Constitution of Organic EL Device

FIG. 1 schematically shows the cross section of an example of an organic EL device generally used in this invention and 1 stands for a substrate, 2 for an anode, 3 for a hole-injecting layer, 4 for a hole-transporting layer, 5 for a light-emitting layer, 6-*a* for a first electron-transporting layer, 6-*b* for a second electron-transporting layer, 7 for an electron-injecting layer, and 8 for a cathode. The organic EL device of this invention comprises the anode, the light-emitting layer, the electron-transporting layer, and the cathode as essential layers and other layers may be provided as needed. Such other layers are, for example, a hole-injecting/transporting layer, an electron-blocking layer, and a hole-blocking layer, but are not limited thereto. The term hole-injecting/transporting layer means a hole-injecting layer and/or a hole-transporting layer. The light-emitting layer, the first electron-transporting layer, and the second electron-transporting layer are arranged sequentially in the aforementioned order.

(2) Substrate

The substrate 1 serves as a support for an organic electroluminescent device and the materials useful therefor include a quartz plate, a glass plate, a metal sheet, a metal foil, a plastic film, and a plastic sheet. In particular, a glass plate and a flat, transparent sheet of synthetic resin such as polyester, polymethacrylate, polycarbonate, and polysulfone are preferred. In the case where a synthetic resin substrate is used, the gas barrier property of the resin needs to be taken into consideration. When the gas barrier property of the substrate is too low, the air passing through the substrate may undesirably deteriorate the organic electroluminescent device. One of the preferred methods for securing the gas barrier property is to provide a dense silicon oxide film or the like at least on one side of the synthetic resin substrate.

(3) Anode

The anode 2 is provided on the substrate 1 and it plays a role of injecting holes into the hole-transporting layer. The anode is usually constructed of a metal such as aluminum, gold, silver, nickel, palladium, and platinum, a metal oxide such as an oxide of indium and/or tin and an oxide of indium and/or zinc, a metal halide such as copper iodide, carbon black, and an electrically conductive polymer such as poly(3-methylthiophene), polypyrrole, and polyaniline. The anode is formed mostly by a process such as sputtering and vacuum deposition. In the case where silver or any other metal, copper iodide, carbon black, an electrically conductive metal oxide, or an electrically conductive polymer is available in fine particles, the anode can be formed by dispersing the particles in a solution of a suitable binder resin and coating the substrate with the dispersion. Further, in the case of an electrically conductive polymer, the anode can be formed in thin film by conducting electrolytic polymerization of the corresponding monomer directly on the substrate 1 or by coating the substrate with the polymer (Appl. Phys. Lett., Vol. 60, p. 2711, 1992). The anode may also be formed by piling different materials one upon another. The thickness of the anode varies with the requirement for transparency. In applications where transparency is required, it is desirable to control the transmission of visible light normally at 60% or more, preferably at 80% or more; in this case, the thickness becomes normally 5-1,000 nm, preferably 10-500 nm. In applications where opaqueness is accepted, the anode may be the same in the transmission as the substrate. Furthermore, a different electrically conductive material can be piled on the aforementioned anode.

(4) Hole-Transporting Layer

The hole-transporting layer 4 is provided on the anode 2 and the hole-injecting layer 3 may be disposed between the two. The condition the material of choice for the hole-transporting layer must satisfy is an ability to inject holes from the anode at high efficiency and transport the injected holes efficiently. This makes it necessary for the material to satisfy the following requirements; low ionization potential, high transparency against visible light, high hole mobility, good stability, and low inclination to generate impurities that become traps of holes during fabrication and use. Still more, since the hole-transporting layer is arranged in contact with the light-emitting layer, the material for the hole-transporting layer must not lower the efficiency by quenching light emitted from the light-emitting layer or forming exciplexes with the light-emitting layer. Besides the aforementioned general requirements, heat resistance is required for applications such as vehicle-mounted display devices. Hence, the material desirably has a Tg of 85° C. or above.

Any of the compounds known thus far as hole-transporting materials may be used as such according to this invention. Examples include aromatic diamines containing two or more tertiary amines whose nitrogen atoms are substituted with two or more condensed aromatic rings (JP Hei 5-234681 A), starburst aromatic amines such as 4,4',4''-tris(1-naphthylphenylamino)triphenylamine (J. Lumin., Vol. 72-74, p. 985, 1997), an aromatic amine consisting of a tetramer of triphenylamine (Chem. Commun., p. 2175, 1996), and Spiro compounds such as 2,2',7,7'-tetrakis(diphenylamino)-9,9'-spirobifluorene (Synth. Metals, Vol. 91, p. 209, 1997). These compounds may be used singly or as a mixture if necessary.

In addition to the aforementioned compounds, examples of the hole-transporting materials include polymeric materials such as polyvinylcarbazole, polyvinyltriphenylamine (JP Hei 7-53953 A), and polyaryleneethersulfone containing tetraphenylbenzidine (Polym. Adv. Tech., Vol. 7, p. 33, 1996).

When the coating process is used for forming the hole-transporting layer, a coating solution is prepared from one kind or two kinds or more of hole-transporting materials of choice and, if necessary, a binder resin which does not become a trap of holes and an additive such as an improver of coating properties, applied to the anode by a process such as spin coating, and dried to form the hole-transporting layer. Examples of the binder resin include polycarbonate, polyarylate, and polyester. As a binder resin lowers the hole mobility when added in a large amount, it had better be added in a small amount, usually 50 wt % or less.

When the vacuum deposition process is used for forming the hole-transporting layer, the hole-transporting material of choice is introduced to a crucible placed in a vacuum container, the container is evacuated to $1 \times 10^{-4}$ Pa or so by a suitable vacuum pump, the crucible is heated to evaporate the hole-transporting material, and the vapor is deposited on the substrate that has an anode formed thereon and is placed opposite the crucible to form the hole-transporting layer. The thickness of the hole-transporting layer is normally 1-300 nm, preferably 5-100 nm. The vacuum deposition process is generally used to form a thin film such as this uniformly.

(5) Hole-Injecting Layer

For the purpose of enhancing still further the hole-injecting efficiency and improving the adhesive strength of the organic layer as a whole to the anode, the hole-injecting layer 3 is disposed between the hole-transporting layer 4 and the anode 2. Disposition of the hole-injecting layer produces an effect of lowering the driving voltage of the device in the initial period and, at the same time, suppressing a rise in voltage during continuous driving of the device at constant current density. The hole-injecting material of choice must satisfy the following requirements; it is formable into a thin film that is uniform in quality and makes good contact with the anode and it is thermally stable, namely, it has a high melting point and a high glass transition temperature. The material is required to have a melting point of 300° C. or above and a glass transition temperature of 100° C. or above. Still more, the material is required to have a low ionization potential to facilitate injection of holes from the anode and show high hole mobility.

The following compounds have been reported to satisfy the aforementioned requirements: phthalocyanine compounds such as copper phthalocyanine (JP Sho 63-295695 A); organic compounds such as polyaniline (Appl. Phys. Lett., Vol. 64, p. 1245, 1994) and polythiophene (Optical Materials, Vol. 9, p. 125, 1998); sputtered carbon membranes (Synth. Met., Vol. 91, p. 73, 1997); metal oxides such as vanadium oxide, ruthenium oxide, and molybdenum oxide (J. Phys. D, Vol. 29, p. 2750, 1996); and p-type organic compounds such as 1,4,5,8-naphthalenetetracarboxylic dianhydride (NTCDA) and hexanitrilehexaazatriphenylene (HAT) (WO2005-109542). These compounds may be used singly or mixed as needed. The hole-injecting layer can also be formed in thin film like the hole-transporting layer and, in the case where the material of choice is an inorganic compound, the process such as sputtering, electron beam deposition, and plasma CVD is used. The thickness of the hole-injecting layer formed as described above is normally 1-300 nm, preferably 5-100 nm.

(6) Light-Emitting Layer

The light-emitting layer 5 is provided on the hole-transporting layer 4. The light-emitting layer may be constituted of a single light-emitting layer or it may be constructed by piling a plurality of light-emitting layers one upon another. The light-emitting layer is constituted of a luminous material or a host material and a fluorescent or phosphorescent material and any of the materials hitherto used for them may be used in this invention.

Examples of the luminous material or the host material include derivatives of condensed ring compounds such as anthracene and pyrene that have been known as luminous substances, metal chelate oxynoid compounds such as tris(8-quinolinolato)aluminum, bisstyryl derivatives such as bis-styrylanthracene derivatives and distyrylbenzene derivatives, tetraphenylbutadiene derivatives, coumarin derivatives, oxadiazole derivatives, pyrrolopyridine derivatives, perinone derivatives, cyclopentadiene derivatives, oxadiazole derivatives, thiadiazolopyridine derivatives, and polymers such as poly(phenylene vinylene) derivatives, poly(para-phenylene) derivatives, and polythiophene derivatives. The luminous materials or the host materials useful for this invention are not limited to the examples given above.

The fluorescent materials to be added to the host materials include derivatives of condensed ring compounds such as perylene and rubrene, quinacridone derivatives, Phenoxazone 660, DCM1, perinone, coumarin derivatives, pyrromethene (diazaindacene) derivatives, and cyanine dyes.

The phosphorescent materials to be added to the host materials are preferably organic metal complexes containing a metal selected from ruthenium, rhodium, palladium, silver, rhenium, osmium, iridium, platinum, and gold, but are not limited thereto. These organic metal complexes are known in the aforementioned patent documents and elsewhere and a suitable substance is selected from them and used in this invention.

Preferable examples of the phosphorescent dopants include complexes containing a noble metal element such as Ir at the center, typically Ir(ppy)$_3$, complexes such as Ir(bt)$_2$.acac3, and complexes such as PtOEt3. Examples of these complexes are shown below, but are not limited thereto.

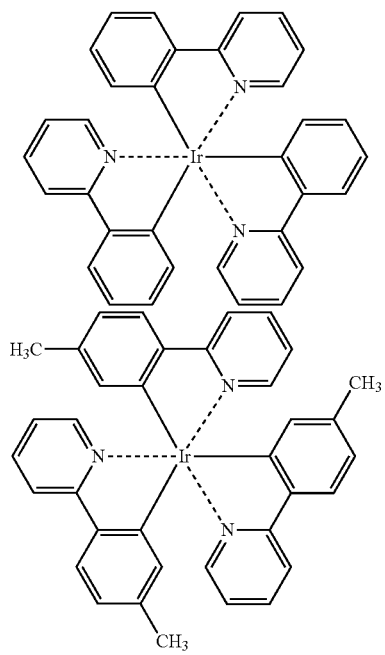

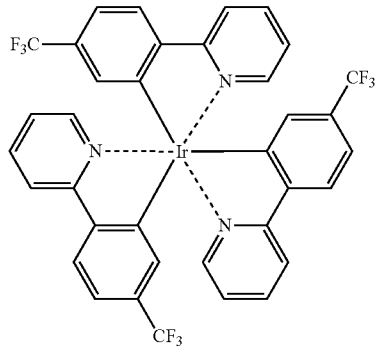
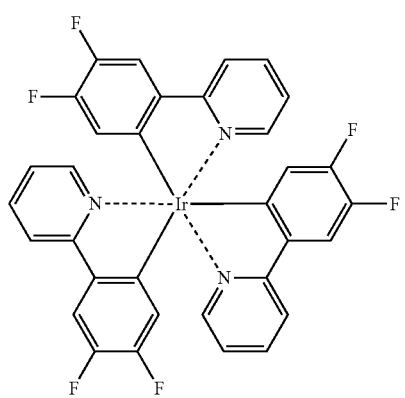
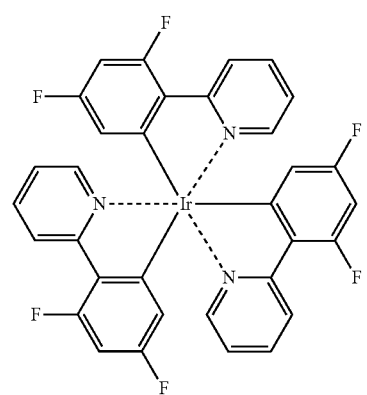
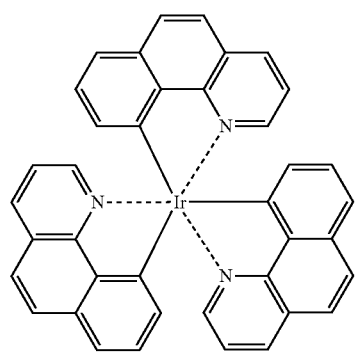
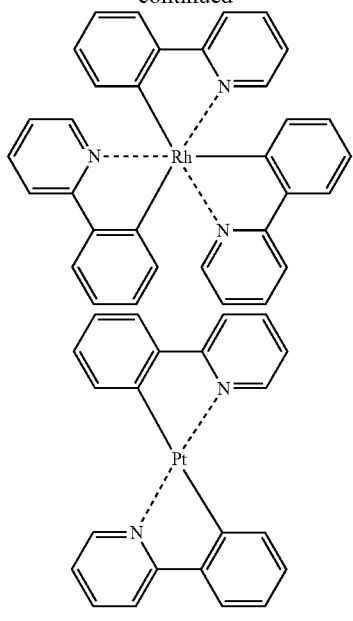
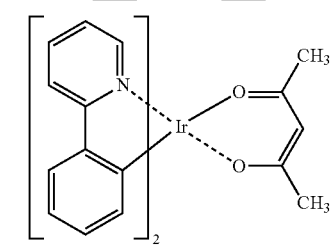
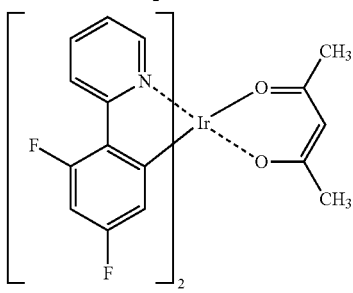
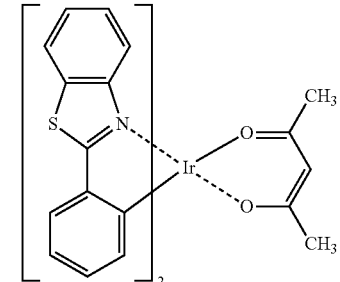
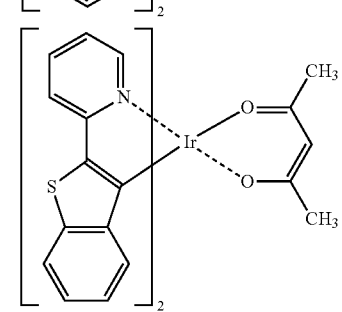

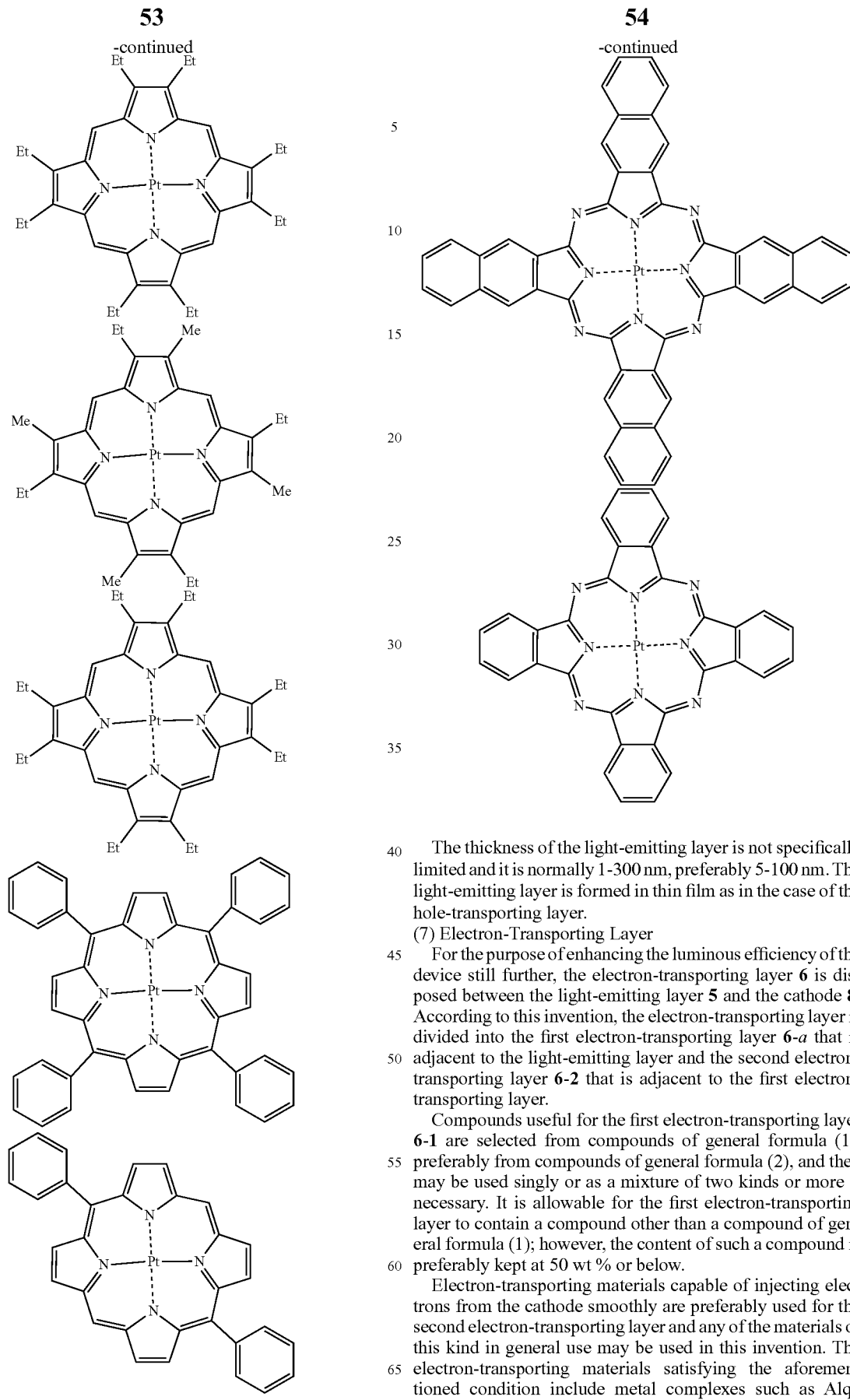

The thickness of the light-emitting layer is not specifically limited and it is normally 1-300 nm, preferably 5-100 nm. The light-emitting layer is formed in thin film as in the case of the hole-transporting layer.

(7) Electron-Transporting Layer

For the purpose of enhancing the luminous efficiency of the device still further, the electron-transporting layer 6 is disposed between the light-emitting layer 5 and the cathode 8. According to this invention, the electron-transporting layer is divided into the first electron-transporting layer 6-*a* that is adjacent to the light-emitting layer and the second electron-transporting layer 6-2 that is adjacent to the first electron-transporting layer.

Compounds useful for the first electron-transporting layer 6-1 are selected from compounds of general formula (1), preferably from compounds of general formula (2), and they may be used singly or as a mixture of two kinds or more if necessary. It is allowable for the first electron-transporting layer to contain a compound other than a compound of general formula (1); however, the content of such a compound is preferably kept at 50 wt % or below.

Electron-transporting materials capable of injecting electrons from the cathode smoothly are preferably used for the second electron-transporting layer and any of the materials of this kind in general use may be used in this invention. The electron-transporting materials satisfying the aforementioned condition include metal complexes such as Alq3 (JP59-194393 A), 10-hydroxybenzo[h]quinoline metal complexes, oxadiazole derivatives, distyrylbiphenyl derivatives, silole derivatives, 3- or 5-hydroxyflavone metal complexes, benzoxazole metal complexes, benzothiazole metal complexes, trisbenzimidazolylbenzene (U.S. Pat. No. 5,645,948), quinoxaline compounds (JP-207169 A), phenanthroline derivatives (JP5-331459 A), 2-t-butyl-9,10-N,N'-dicyanoanthraquinonediimine, n-type hydrogenated amorphous silicon carbide, n-type zinc sulfide, and n-type zinc selenide.

Of the aforementioned compounds useful for the second electron-transporting layer, quinolinol-based metal complexes are particularly preferred.

Examples of the metals at the center of the quinolinol-based metal complexes include lithium, beryllium, magnesium, aluminum, gallium, and zinc. The ligand quinolinol may be unsubstituted or arbitrarily substituted. The thickness of each of the first and second electron-transporting layers is normally 1-300 nm, preferably 5-100 nm. The first electron-transporting layer is formed on the light-emitting layer by coating or vacuum deposition as in the case of the hole-transporting layer and the vacuum deposition process is usually employed. Similarly, the second electron-transporting layer is formed on the first electron-transporting layer.

(8) Cathode

The cathode 8 plays a role of injecting electrons into the light-emitting layer 5. A material useful for the cathode may be the same as the aforementioned material for the anode 2. However, a metal of low work function is desirable for efficient injection of electrons and a metal such as tin, magnesium, indium, calcium, aluminum, and silver or any of alloys thereof may be used. Specific examples are electrodes made from alloys of low work function such as magnesium-silver alloys, magnesium-indium alloys, and aluminum-lithium alloys.

The thickness of the cathode is usually the same as that of the anode. For the purpose of protecting the cathode made from a metal of low work function, covering the cathode with a metal of high work function that is stable against the air improves the stability of the device. A metal such as aluminum, silver, copper, nickel, chromium, gold, and platinum is used for this purpose.

Further, disposition of the electron-injecting layer 7 in the form of an ultrathin insulating film (0.1-5 nm) of LiF, $MgF_2$, $Li_2O$, or the like between the cathode 8 and the electron-transporting layer 6 is also an effective method for enhancing the efficiency of the device.

It is possible to fabricate a device with a structure that is the reverse of the structure shown in FIG. 1; that is, the device is fabricated by piling the cathode 8, the electron-transporting layer 7, the second electron-transporting layer 6-b, the first electron-transporting layer 6-a, the light-emitting layer 5, the hole-transporting layer 4, the hole-injecting layer 3, and the cathode 2 one upon another in this order on the substrate 1. As described earlier, it is also possible to dispose the organic EL device of this invention between two substrates at least one of which is highly transparent. In this case of the reverse structure, it is also possible to add or omit a layer or layers as needed.

The organic EL device of this invention is applicable to a single device, a device with its structure arranged in array, or a device in which the anode and the cathode are arranged in X-Y matrix. According to this invention, a combination of the first electron-transporting layer containing a compound of specified skeleton with the second electron-transporting layer containing an existing electron-transporting material other than the said compound of specified skeleton or a material comparable to the existing material provides an organic EL device that can perform at enhanced luminous efficiency with markedly improved driving stability even at low voltage. The organic EL device thus obtained displays excellent performance when applied to full-color or multicolor panels.

EXAMPLES

This invention will be described in more detail below with reference to the example, but will not be limited thereto. This invention can be reduced to practice in various modes unless such practice exceeds the substance of this invention.

Synthetic Example 1

Synthesis of indolo[2,3-a]carbazole

In a 2,000-ml three-necked flask that had been deaerated and filled with nitrogen were placed 33.3 g (297.0 millimoles) of 1,2-cyclohexanedione, 86.0 g (594.7 millimoles) of phenylhydrazine hydrochloride, and 1,000 ml of ethanol and stirred. To this mixture was added dropwise 3.0 g (30.6 millimoles) of concentrated sulfuric acid over 5 minutes and, upon completion of the dropwise addition, the mixture was stirred at 65° C. for 4 hours. The mixture was cooled to room temperature and the purplish brown crystals formed were collected by filtration and washed twice by reslurrying in 500 ml of ethanol. The crystals were dried under reduced pressure to strip off the solvent and 80.0 g of a purplish brown powder was obtained.

Then, 72.0 g (261.5 millimoles) of the purplish brown powder obtained above was placed in a 1,000-ml three-necked flask, 720 g of acetic acid and 72.0 g (631 millimoles) of trifluoroacetic acid were further added to the flask, and the mixture was stirred at 100° C. for 15 hours. The mixture was cooled to room temperature and the crystals formed were collected by filtration, rinsed with 200 ml of acetic acid, and further rinsed with 200 ml of hexane. The mixture was dried under reduced pressure to strip off the solvent and 30.0 g (117.1 millimoles, 39.4% yield) of indolo[2,3-a]carbazole was obtained as a white powder.

Synthetic Example 2

Synthesis of 11-phenylindolo[2,3-a]carbazole

In a 1,000-ml three-necked flask that had been deaerated and filled with nitrogen were placed 26.0 g (101.4 millimoles) of indolo[2,3-a]carbazole, 122.7 g (601.4 millimoles) of iodobenzene, 54.7 g (287.2 millimoles) of copper iodide, 66.7 g (482.6 millimoles) of potassium carbonate, and 800 ml of quinoline and the mixture was stirred at 190° C. for 72 hours. The mixture was cooled to room temperature, 500 ml of water and 500 ml of dichloromethane were added, and the yellow crystals formed were filtered off. The filtrate was separated into an organic layer and an aqueous layer and the organic layer was washed three times with 500 ml of water. The organic layer was dried over magnesium sulfate, the magnesium sulfate was filtered off, and the solvent was stripped off under reduced pressure. The residue was purified by silica gel column chromatography to yield 13.7 g (41.2 millimoles, 40.6% yield) of 11-phenylindolo[2,3-a]carbazole as a white powder.

Synthetic Example 3

Synthesis of indol[3,2-b]carbazole

In a 2,000-ml three-necked flask that had been deaerated and filled with nitrogen were placed 50.69 g (205.8 millimoles) of 3,3'-methylenediindole and 30.55 g (206.1 millimoles) of triethyl orthoformate, then 640 g of methanol was added, and the mixture was stirred. To this mixture was added dropwise 5.0 g (51.5 millimoles) of concentrated sulfuric acid over 3 minutes and the mixture was heated under reflux for 1 hour. The mixture was cooled to room temperature and the reddish-brown crystals formed were collected by filtration and washed twice by reslurrying in 500 ml of methanol. The solvent was stripped off under reduced pressure and 36.8 g (143.8 millimoles, 69.9% yield) of indolo[3,2-b]carbazole was obtained as a reddish-brown powder.

Synthetic Example 4

Synthesis of Illustrated Compound A-19

In a 2,000-ml three-necked flask that had been deaerated and filled with nitrogen were placed 2.18 g (50.0 millimoles) of sodium hydride (55% dispersion) and 70 ml of dehydrated DMF and the mixture was stirred under nitrogen flow. To this mixture was added dropwise a solution of 13.5 g (40.6 millimoles) of 11-phenylindolo[2,3-a]carbazole in 150 ml of dehydrated DMF over 10 minutes and, upon completion of the dropwise addition, the mixture was stirred for 1 hour. Then, a solution of 10.4 g (39.0 millimoles) of 2-chloro-4,6-diphenyl-1,3,5-triazine in 150 ml of dehydrated DMF was added dropwise over 1 hour. Upon completion of the dropwise addition, the stirring was continued for 3 hours, then 600 g of water was added, and the crystals separated were collected by filtration. The crystals were washed twice by reslurrying in 300 g of water, then further washed by reslurrying in 300 g of methanol. The solvent was stripped off under reduced pressure and 21.0 g of yellow crystals was obtained. The crystals were purified by crystallization from THF and methanol, the solvent was stripped off under reduced pressure, and 12.7 g (22.5 millimoles, 55.4% yield) of Illustrated Compound A-19 was obtained as a yellow solid.

APCI-MS, m/z 564 [M+1]$^+$; melting point, 263° C.; glass transition temperature (Tg), 131° C.

Synthetic Example 5

Synthesis of Illustrated Compound D-5

In a 2,000-ml three-necked flask that had been deaerated and filled with nitrogen were placed 4.36 g (100.0 millimoles) of sodium hydride (55% dispersion) and 70 ml of dehydrated DMF and the mixture was stirred under nitrogen flow. To this mixture was added dropwise a solution of 10.4 g (40.6 millimoles) of indolo[3,2-b]carbazole in 150 ml of dehydrated DMF over 10 minutes and, upon completion of the dropwise addition, the mixture was stirred for 1 hour. Then, a solution of 20.9 g (78.0 millimoles) of 2-chloro-4,6-diphenyl-1,3,5-triazine in 300 ml of dehydrated DMF was added dropwise over 1 hour. Upon completion of the dropwise addition, the stirring was continued for 3 hours, then 900 g of water was added, and the crystals separated were collected by filtration. The crystals were washed twice by reslurrying in 450 g of water and then further washed by reslurrying in 450 g of methanol. The solvent was stripped off under reduced pressure and 42.0 g of brown crystals was obtained. The crystals were purified by crystallization from THF and methanol, the solvent was stripped under reduced pressure, and 13.4 g (18.6 millimoles, 46% yield) of Illustrated Compound D-5 was obtained as a light brown solid.

APCI-MS, m/z 719 [M+1]$^+$; melting point, 498° C.; Tg, not observed.

Synthetic Example 6

Synthesis of Illustrated Compound D-7

In a 200-ml three-necked flask that had been deaerated and filled with nitrogen were placed 1.3 g (5.1 millimoles) of indolo[3,2-b]carbazole, 1.4 g (14.6 millimoles) of sodium tert-butoxide, 8.2 mg of palladium acetate (0.037 millimole), and 80 ml of xylene and the mixture was stirred at room temperature for 1 hour. To this mixture was added 64.0 mg (0.32 millimole) of tri-tert-butylphosphine and the mixture was heated at 120° C. for 40 hours with stirring. The mixture was cooled to room temperature, 70 ml of water was added, and the solid separated was collected by filtration. The solid was purified by reslurrying successively in methanol, toluene, and chloroform with application of heat to yield 1.0 g (1.4 millimoles, 27.5% yield) of Illustrated Compound D-7 as a light brown solid.

APCI-MS, m/z 715 [M+1]$^+$; melting point, 426° C.; Tg, not observed.

Synthetic Example 7

Synthesis of Illustrated Compound B-19

In a 1,000-ml three-necked flask that had been deaerated and filled with nitrogen were placed 2.2 g (56.0 millimoles) of 55% sodium hydride (55% dispersion) and 240 ml of dehydrated DMF and the mixture was stirred under nitrogen flow. To this mixture was added dropwise a solution of 13.3 g (40.0 millimoles) of 11-phenylindolo[2,3-a]carbazole in 25 ml of dehydrated DMF over 10 minutes and, upon completion of the dropwise addition, the mixture was stirred for 1 hour. Then, a solution of 8.8 g (48.0 millimoles) of 2,4,6-trichloro-1,3,5-triazine in 150 ml of dehydrated DMF was added dropwise over 1 hour. Upon completion of the dropwise addition, the stirring was continued for 3 hours, then 500 ml of water was added, and the crystals separated were collected by filtration. The crystals were washed twice by reslurrying in 300 g of water and then further washed by reslurrying in 300 g of methanol. The solvent was stripped off under reduced pressure and 18.2 g of light yellow crystals was obtained. The crystals were used in the next reaction without purification.

In a 2,000-ml three-necked flask were placed 18.2 g (38.0 millimoles) of the light yellow crystals, 9.7 g (80.0 millimoles) of phenylboronic acid, 1.8 g (1.6 millimoles) of tetrakis(triphenylphosphine)palladium, 150 ml of ethanol, and 450 ml of toluene and the mixture was stirred. Then, a solution of 29.8 g (280.0 millimoles) of sodium carbonate in 140 ml of water was added and the mixture was stirred at 85° C. for 4 hours. The mixture was cooled to room temperature, 200 ml of water and 200 ml of toluene were added, the mixture was separated into an organic layer and an aqueous layer, and the organic layer was washed with 200 ml of water. The organic layer was dehydrated over magnesium sulfate, the magnesium sulfate was filtered off, and the solvent was stripped off under reduced pressure. The residue was purified by crystallization from dichloromethane and ethanol, the solvent was stripped off under reduced pressure, and 5.2 g (9.2 millimoles, 23% yield) of Illustrated Compound B-19 was obtained as a white solid.

APCI-MS, m/z 563 [M+1]$^+$; melting point, 252° C.; Tg, 127° C.

Synthetic Example 8

Synthesis of Illustrated Compound A-9

In a 100-ml three-necked flask that had been deaerated and filled with nitrogen was placed a solution of 0.21 g (0.94 millimole) of palladium(II) acetate, 0.76 g (3.8 millimoles) of tri-tert-butylphosphine was added, and the mixture was heated at 60° C. with stirring for 30 minutes. The resulting solution was transferred under nitrogen flow to a solution heated at 60° C. of 4.6 g (18.0 millimoles) of indolo[2,3-a]carbazole, 5.8 g (18.0 millimoles) of 3-carbazolylbromobenzene, and 7.7 g (80.0 millimoles) of sodium tert-butoxide in 180 ml of xylene. The solution was then heated to 130° C., and heated with stirring at this temperature for 5 hours. The solution was cooled to room temperature and 200 ml of water was added. The mixture was subjected to oil-water separation, and the organic layer was concentrated under reduced pressure to give a crude product. The crude product was purified by crystallization from dichloromethane and ethanol, the solvent was stripped off under reduced pressure, and 4.2 g (8.4 millimoles, 47% yield) of 11-(4-carbazolylphenyl)indolo[2,3-a]carbazole was obtained.

Next, 0.42 g (9.6 millimoles) of sodium hydride (55% dispersion) and 10 ml of dehydrated DMF were placed in a 200-ml three-necked flask that had been deaerated and filled with nitrogen and the mixture was stirred under nitrogen flow. To this mixture was added dropwise a solution of 4.0 g (8.0 millimoles) of 11-(4-carbazolylphenyl)indolo[2,3-a]carbazole obtained above in 20 ml of dehydrated DMF over 10 minutes. Upon completion of the dropwise addition, the mixture was stirred for 1 hour or so. A solution of 2.1 g (8.0 millimoles) of 2-chloro-4,6-diphenyl-1,3,5-triazine in 20 ml of dehydrated DMF was added dropwise over 1 hour. Upon completion of the dropwise addition, the mixture was stirred for 3 hours, 100 g of water was added, and the crystals separated were collected by filtration. The crystals were washed twice by reslurrying in 100 g of water and further washed by reslurrying in 100 g of methanol. The solvent was stripped off under reduced pressure and yellow crystals were obtained. The crystals were purified by crystallization from THF/methanol and 3.0 g (4.1 millimoles, 51% yield) of Illustrated Compound A-9 was obtained as a yellow solid.

APCI-MS, m/z 729 [M+1]$^+$; melting point, 319° C.; Tg, 168° C.

Synthetic Example 9

Synthesis of Illustrated Compound A-17

In a 2,000-ml three-necked flask that had been deaerated and filled with nitrogen were placed 4.8 g (110.0 millimoles) of sodium hydride (55% dispersion) and 70 ml of dehydrated DMF and the mixture was stirred under nitrogen flow. To this mixture was added dropwise a solution of 13.5 g (52.7 millimoles) of indolo[2,3-a]carbazole in 150 ml of dehydrated DMF over 10 minutes and, upon completion of the dropwise addition, the mixture was stirred for 1 hour or so. Then, a solution of 29.4 g (110.0 millimoles) of 2-chloro-4,6-diphenyl-1,3,5-triazine in 150 ml of dehydrated DMF was added dropwise over 1 hour. Upon completion of the dropwise addition, the stirring was continued for 3 hours, then 900 g of water was added, and the crystals separated were collected by filtration. The crystals were washed twice by reslurrying in 450 g of water and then further washed by reslurrying in 450 g of methanol. The solvent was stripped off under reduced pressure and 35.0 g of crystals was obtained. The crystals were purified by crystallization from THF/methanol and 24.0 g (33.4 millimoles, 63.4% yield) of Illustrated Compound A-17 was obtained as a yellow solid.

APCI-MS, m/z 719 [M+1]$^+$; melting point, 426° C.; Tg, not observed.

Synthetic Example 10

Synthesis of Illustrated Compound C-19

In a 50-ml three-necked flask that had been deaerated and filled with nitrogen was placed a solution of 0.071 g (0.32 millimole) of palladium(II) acetate in 5 ml of xylene, 0.32 ml (1.3 millimoles) of tri-tert-butylphosphine was added, and the mixture was heated at 60° C. with stirring for 30 minutes. This solution was transferred to a solution heated at 60° C. of 2.0 g (6.0 millimoles) of 11-phenylindolo[2,3-a]carbazole, 2.5 g (6.9 millimoles) of 2,6-diphenyl-4-iodopyridine, and 2.6 g (26.7 millimoles) of sodium tert-butoxide in 60 ml of xylene under nitrogen flow. The solution was then heated to 130° C. and heated with stirring at this temperature for 5 hours. The solution was cooled to room temperature and 70 ml of water was added. The mixture was subjected to oil-water separation, the organic layer was concentrated under reduced pressure, and 4.85 g of a crude product was obtained. The crude product was purified by crystallization from dichloromethane and ethanol, the solvent was stripped off under reduced pressure, and 1.4 g (2.5 millimoles, 36% yield) of Illustrated Compound C-19 was obtained as a white solid.

APCI-MS, m/z 562 [M+1]$^+$; melting point, 277° C., 287° C.; Tg, 130° C.

Example 1

With reference to FIG. 1, the constituent layers were deposited in thin film one upon another by the vacuum deposition process at a degree of vacuum of $1.0 \times 10^{-5}$ Pa on a glass substrate on which a 110 nm-thick ITO anode had been formed. First, CuPc (copper phthalocyanine) was deposited on the ITO anode to a thickness of 25 nm as a hole-injecting layer. Then, NPB [4,4'-bis(N-(1-naphthyl)-N-phenylamino)biphenyl] was deposited to a thickness of nm as a hole-transporting layer. Then, BAlq [p-phenylphenolato-bis(2-methyl-8-quinolinolato)aluminum] and Ir(piq)3[tris(1-phenylisoquinoline)iridium complex] were co-deposited as a light-emitting layer on the hole-transporting layer to a thickness of 45 nm from different evaporation sources while controlling the content of Ir(piq)$_3$ at 4.0 wt %. Thereafter, Illustrated Compound A-19 was deposited as a first electron-transporting layer to a thickness of 10 nm and Alq3 [tris(8-quinolinolato)aluminum complex] was deposited as a second electron-transporting layer to a thickness of 20 nm. Still further, LiF (lithium fluoride) was deposited as an electron-injecting layer on the electron-transporting layer to a thickness of 0.5 nm. Finally, Al (aluminum) was deposited as a cathode on the electron-injecting layer to a thickness of 100 nm to complete the fabrication of an organic EL device.

Example 2

An organic EL device was fabricated as in Example 1 with the exception of controlling the thicknesses of the first and second electron-transporting layers respectively at 20 nm and 10 nm.

Comparative Example 1

An organic EL device was fabricated as in Example 1 with the exception of omitting the first electron-transporting layer and controlling the thickness of the second electron-transporting layer at 30 nm.

The organic EL devices thus fabricated were respectively connected to an outside power source and, upon application of direct current voltage, they emitted light with the characteristics shown in Table 1. In Table 1, the driving voltage and current efficiency were measured at 200 A/m$^2$ and the LT50 at 400 A/m$^2$. The maximum wavelength of the spectrum of light emitted from the device is 620 nm and this proves that light is emitted from Ir(pig)3.

TABLE 1

|  | Driving voltage (V) | Current efficiency (cd/A) | LT50 (hr) |
| --- | --- | --- | --- |
| Example1 | 10.8 | 6.5 | 1200 |
| Example2 | 10.3 | 6.6 | 1500 |
| Comparative example1 | 11.0 | 6.4 | 800 |

As is apparent from Table 1, the devices of Examples 1 and 2 have attained lower voltage, higher efficiency, and longer lifetime than the device of Comparative Example 1.

Example 3

With reference to FIG. 1, the constituent layers were deposited in thin film one upon another by the vacuum deposition process at a degree of vacuum of 1.0×10$^{-5}$ Pa on a glass substrate on which a 110 nm-thick ITO anode had been formed. First, CuPc was deposited as a hole-injecting layer on the ITO anode to a thickness of 25 nm. Then, NPB was deposited as a hole-transporting layer to a thickness of 45 nm. Then, Alq3 was deposited as a light-emitting layer on the hole-transporting layer to a thickness of 20 nm. Thereafter, Compound A-19 was deposited as a first electron-transporting layer to a thickness of 10 nm and Alq3 was deposited as a second electron-transporting layer to a thickness of 30 nm. Still further, LiF was deposited as an electron-injecting layer on the electron-transporting layer to a thickness of 0.5 nm. Finally, Al was deposited as a cathode on the electron-injecting layer to a thickness of 100 nm to complete the fabrication of an organic EL device.

Example 4

An organic EL device was fabricated as in Example 3 with the exception of controlling the thicknesses of the first and second electron-transporting layers respectively at 30 nm and 10 nm.

Comparative Example 2

An organic EL device was fabricated as in Example 3 with the exception of omitting the first electron-transporting layer and controlling the thickness of the second electron-transporting layer at 40 nm.

The organic EL devices thus fabricated were respectively connected to an outside power source and, upon application of direct current voltage, they emitted light with the characteristics shown in Table 2. In Table 2, the driving voltage and current efficiency were measured at 200 A/m$^2$ and the LT50 at 400 A/m$^2$. The maximum wavelength of the spectrum of light emitted from the device is 520 nm and this proves that light is emitted from Alq3.

TABLE 2

|  | Driving voltage (V) | Current efficiency (cd/A) | LT50 (hr) |
| --- | --- | --- | --- |
| Example3 | 6.4 | 3.9 | 1300 |
| Example4 | 5.6 | 3.8 | 2000 |
| Comparative example2 | 6.5 | 3.6 | 1000 |

As is apparent from Table 2, the devices of Examples 3 and 4 have attained lower voltage, higher efficiency, and longer lifetime than the device of Comparative Example 2.

INDUSTRIAL APPLICABILITY

The organic EL device of this invention can attain high efficiency and long lifetime even at low voltage by using a specified compound as a partial constituent of the electron-transporting layer. Furthermore, in a device that uses a phosphorescent dopant in the light-emitting layer, the lowest triplet energy level of the compound is sufficiently high to confine the lowest triplet energy level of the phosphorescent molecule and, as a result, no energy flows out of the light-emitting layer and high efficiency and long lifetime can be attained.

The organic EL device of this invention is at a level satisfactory for practical use in respect to luminous characteristics, driving stability, and durability and is of high technical value for its applicability to flat panel displays (mobile phone display devices, vehicle-mounted display devices, office computer display devices, and television sets), light sources utilizing the characteristics of planar light emitters (illumination, light sources of copiers, and backlight sources of liquid crystal displays and instruments), signboards, and beacon lights.

The invention claimed is:

1. An organic electroluminescent device comprising at least a light-emitting layer and an electron-transporting layer between an anode and a cathode facing each other wherein the electron-transporting layer consists of a first electron-transporting layer and a second electron-transporting layer, the first electron-transporting layer and the second electron-transporting layer are arranged sequentially in this order from the side of the light-emitting layer to the side of the cathode, and the first electron-transporting layer contains a compound represented by the following general formula (1):

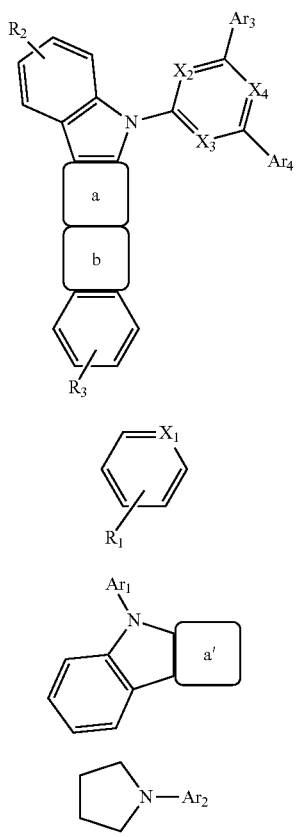

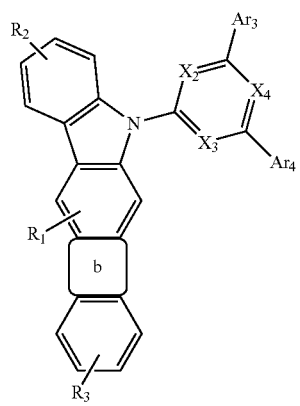

wherein ring a is an aromatic or heterocyclic ring fused to two adjacent rings and represented by formula (a1) or (a2), ring a' is an aromatic or heterocyclic ring fused to three adjacent rings and represented by formula (a1), $X_1$ is CH or N, and ring b is a heterocyclic ring fused to two adjacent rings and represented by formula (b1); $Ar_1$ to $Ar_4$ each is independently a substituted or unsubstituted aromatic hydrocarbon group or a substituted or unsubstituted aromatic heterocyclic group, wherein the unsubstituted aromatic hydrocarbon groups are aromatic hydrocarbon groups of 6-10 carbon atoms, and the unsubstituted aromatic heterocyclic groups are aromatic heterocyclic groups of 2-5 carbon atoms, in the case where the aromatic hydrocarbon groups or aromatic heterocyclic groups contain substituents, said substituents are selected from the group consisting of an alkyl group of 1-10 carbon atoms, an aralkyl group of 4-15 carbon atoms, an alkoxyl group of 1-15 carbon atoms, an amino group, an aromatic hydrocarbon group of 6-18 carbon atoms, and an aromatic heterocyclic group of 3-17 carbon atoms; $R_1$ to $R_3$ each is independently a hydrogen atom, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group; $X_2$, $X_3$, and $X_4$ each is independently CH or N and at least one of them is N.

2. An organic electroluminescent device as described in claim 1 wherein the compound represented by general formula (1) is a compound represented by the following general formula (2):

wherein ring b, $Ar_2$ to $Ar_4$, $R_1$ to $R_3$, and $X_2$ to $X_4$ respectively have the same meaning as ring b, $Ar_2$ to $Ar_4$, $R_1$ to $R_3$, and $X_2$ to $X_4$ in general formula (1).

3. An organic electroluminescent device as described in claim 1 or 2 wherein, in general formula (1) or (2), one of $X_2$ to $X_4$ is a nitrogen atom.

4. An organic electroluminescent device as described in claim 3 wherein, $X_4$ is a nitrogen atom.

5. An organic electroluminescent device as described in claim 1 or 2 wherein, in general formula (1) or (2), two of $X_2$ to $X_4$ are nitrogen atoms.

6. An organic electroluminescent device as described in claim 5 wherein, in general formula (1) or (2), $X_2$ and $X_3$ are nitrogen atoms.

7. An organic electroluminescent device as described in claim 1 or 2 wherein, in general formula (1) or (2), all of $X_2$ to $X_4$ are nitrogen atoms.

8. An organic electroluminescent device as described in claim 1 or 2 wherein, in general formula (1) or (2), $Ar_1$ to $Ar_4$ each is independently a substituted or unsubstituted aromatic hydrocarbon group of 6-10 carbon atoms or a substituted or unsubstituted aromatic heterocyclic group of 2-5 carbon atoms.

9. An organic electroluminescent device as described in claim 1 or 2 wherein, in general formula (1) or (2), $R_1$ to $R_3$ each is independently a hydrogen atom, a substituted or unsubstituted aromatic hydrocarbon group of 6-18 carbon atoms or a substituted or unsubstituted aromatic heterocyclic group of 3-17 carbon atoms.

10. An organic electroluminescent device as described in claim 1 or 2 wherein the second electron-transporting layer contains a quinolinol-based metal complex.

11. The organic electroluminescent device according to claim 1, wherein the light-emitting layer comprises a host material selected from the group consisting of derivatives of condensed ring compounds, metal chelate oxynoid compounds, bisstyryl derivatives, tetraphenylbutadiene derivatives, coumarin derivatives, oxadiazole derivatives, pyrrolopyridine derivatives, perinone derivatives, cyclopentadiene derivatives, oxadiazole derivatives, thiadiazolopyridine derivatives, poly(phenylene vinylene) derivatives, poly(paraphenylene) derivatives, and polythiophene derivatives.

* * * * *